United States Patent
Fischer et al.

(10) Patent No.: US 8,658,570 B2
(45) Date of Patent: *Feb. 25, 2014

(54) USE OF ANTHRANILAMIDE DERIVATIVES FOR CONTROLLING INSECTS AND SPIDER MITES BY DRENCHING, SOIL MIXING, FURROW TREATMENT, DRIP APPLICATION, SOIL, STEM OR FLOWER INJECTION, IN HYDROPONIC SYSTEMS, BY PLANTING HOLE TREATMENT OR DIP APPLICATION, FLOATING OR SEEDBOX APPLICATION OR BY TREATING SEED, AND ALSO FOR ENHANCING THE STRESS TOLERANCE OF PLANTS TO ABIOTIC STRESS

(75) Inventors: Rüdiger Fischer, Pulheim (DE); Christian Funke, Leichlingen (DE); Christoph Grondal, Köln (DE); Ernst Rudolf Gesing, Erkrath (DE); Heinz-Juergen Wroblowsky, Langenfeld (DE); Wolfram Andersch, Bergisch Gladbach (DE); Olga Malsam, Rösrath (DE); Peter Lösel, Leverkusen (DE); Udo Reckmann, Köln (DE); Christopher Hugh Rosinger, Hofheim (DE); Heike Hungenberg, Langenfeld (DE)

(73) Assignee: Bayer Cropscience AG, Monheim (DE)

( * ) Notice: Subject to any disclaimer, the term of this patent is extended or adjusted under 35 U.S.C. 154(b) by 50 days.

This patent is subject to a terminal disclaimer.

(21) Appl. No.: 13/186,129

(22) Filed: Jul. 19, 2011

(65) Prior Publication Data

US 2012/0022112 A1 Jan. 26, 2012

Related U.S. Application Data

(60) Provisional application No. 61/365,819, filed on Jul. 20, 2010.

(30) Foreign Application Priority Data

Jul. 20, 2010 (EP) .................................. 10170154

(51) Int. Cl.
| | | |
|---|---|---|
| A01N 43/40 | (2006.01) | |
| A61K 31/44 | (2006.01) | |
| A01N 43/56 | (2006.01) | |
| A61K 31/415 | (2006.01) | |

(52) U.S. Cl.
USPC .......................................... 504/341; 514/406

(58) Field of Classification Search
USPC ................................. 514/341, 406
See application file for complete search history.

(56) References Cited

U.S. PATENT DOCUMENTS

| | | | |
|---|---|---|---|
| 4,785,002 A | 11/1988 | Draber et al. | |
| 5,201,931 A | 4/1993 | Abrams et al. | |
| 7,241,936 B2 | 7/2007 | Babiychuk et al. | |
| 8,324,390 B2 * | 12/2012 | Fischer et al. | 546/275.4 |
| 2010/0029478 A1 * | 2/2010 | Alig et al. | 504/100 |
| 2010/0292226 A1 * | 11/2010 | Funke et al. | 514/229.2 |
| 2011/0275676 A1 * | 11/2011 | Fischer et al. | 514/338 |
| 2011/0306645 A1 * | 12/2011 | Fischer et al. | 514/341 |
| 2011/0311503 A1 * | 12/2011 | Funke et al. | 424/93.46 |
| 2011/0312953 A1 * | 12/2011 | Fischer et al. | 514/230.5 |
| 2012/0010073 A1 * | 1/2012 | Funke et al. | 504/100 |
| 2012/0010249 A1 * | 1/2012 | Fischer et al. | 514/341 |
| 2012/0010250 A1 * | 1/2012 | Fischer et al. | 514/341 |
| 2012/0015980 A1 * | 1/2012 | Fischer et al. | 514/333 |
| 2012/0094830 A1 * | 4/2012 | Alig et al. | 504/100 |

FOREIGN PATENT DOCUMENTS

| | | | |
|---|---|---|---|
| DE | 3534948 | 4/1987 | |
| DE | 277832 | 4/1990 | |
| DE | 277835 | 4/1990 | |
| DE | 4103253 | 8/1992 | |
| DE | 2007/144100 | * 12/2007 | ........... C07D 401/14 |
| WO | 0004173 | 1/2000 | |
| WO | 0028055 | 5/2000 | |

* cited by examiner

*Primary Examiner* — Sean Basquill
(74) *Attorney, Agent, or Firm* — Miles & Stockbridge P.C.

(57) ABSTRACT

The present invention relates to the use of anthranilamide derivatives of the general formula (I)

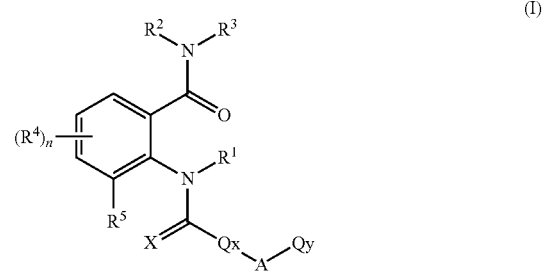

—in which $R^1$, $R^2$, $R^3$, $R^4$, $R^5$, A, X, Qx, Qy and n have the general meanings given in the description—for controlling insects and/or spider mites by drenching, soil mixing, furrow treatment, droplet application, in hydroponic systems, by planting hole treatment, soil, stem or flower injection, dip application, floating or seedbox application or by treating seed, and also for enhancing the stress tolerance of plants to abiotic stress.

14 Claims, No Drawings

USE OF ANTHRANILAMIDE DERIVATIVES FOR CONTROLLING INSECTS AND SPIDER MITES BY DRENCHING, SOIL MIXING, FURROW TREATMENT, DRIP APPLICATION, SOIL, STEM OR FLOWER INJECTION, IN HYDROPONIC SYSTEMS, BY PLANTING HOLE TREATMENT OR DIP APPLICATION, FLOATING OR SEEDBOX APPLICATION OR BY TREATING SEED, AND ALSO FOR ENHANCING THE STRESS TOLERANCE OF PLANTS TO ABIOTIC STRESS

CROSS REFERENCE TO RELATED APPLICATIONS

This application claims priority to European Application No. 10170154.8 filed Jul. 20, 2010 and U.S. Provisional Application No. 61/365,819 filed Jul. 20, 2010, the contents of which are incorporated by reference in their entireties.

BACKGROUND

1. Field of the Invention

The present invention relates to the use of anthranilamide derivatives for controlling insects and/or spider mites and/or nematodes by drenching, soil mixing, furrow treatment, drip application, in hydroponic systems, planting hole treatment, soil, stem or flower injection, dip application, floating or seedbox application or by treating seed.

The present invention also relates to the use of anthranilamide derivatives for enhancing the stress tolerance of plants to abiotic stress, in particular for enhancing plant growth and/or for increasing plant yield and/or for increasing the tolerance to drought and dry conditions. It is known that plants react to natural stress conditions such as, for example, cold temperatures, heat, dry conditions, injury, attack by pathogens (viruses, bacteria, fungi, insects) etc, but also to herbicides, with specific or unspecific defence mechanisms [Pflanzenbiochemie, pp. 393-462, Spektrum Akademischer Verlag, Heidelberg, Berlin, Oxford, Hans W. Heldt, 1996; Biochemistry and Molecular Biology of Plants, pp. 1102-1203, American Society of Plant Physiologists, Rockville, Md., eds. Buchanan, Gruissem, Jones, 2000].

2. Description of Related Art

Numerous proteins, and the genes which code for them, which are involved in defence reactions to abiotic stress (for example cold temperatures, heat, dry conditions, salt, flooding), are known to be present in plants. Some of these form part of signal transduction chains (for example transcription factors, kinases, phosphatases) or cause a physiological response of the plant cell (for example ion transport, deactivation of reactive oxygen species). The signalling chain genes of the abiotic stress reaction include transcription factors of the DREB and CBF classes (Jaglo-Ottosen et al., 1998, Science 280: 104-106). The reaction to salinity stress involves phosphatases of the ATPK and MP2C types. In addition, in the event of salinity stress, the biosynthesis of osmolytes such as proline or sucrose is often activated. This involves, for example, sucrose synthase and proline transporter (Hasegawa et al., 2000, Annu Rev Plant Physiol Plant Mol Biol 51: 463-499). The stress defence of the plants to cold and drought uses some of the same molecular mechanisms. There is a known accumulation of what are called late embryogenesis abundant proteins (LEA proteins), which include the dehydrins as an important class (Ingram and Bartels, 1996, Annu Rev Plant Physiol Plant Mol Biol 47: 277-403, Close, 1997, Physiol Plant 100: 291-296). These are chaperones which stabilize vesicles, proteins and membrane structures in stressed plants (Bray, 1993, Plant Physiol 103: 1035-1040). In addition, there is frequently induction of aldehyde dehydrogenases, which deactivate the reactive oxygen species (ROS) which form in the event of oxidative stress (Kirch et al. 2005. Plant Mol Biol 57: 315-332).

Heat shock factors (FISF) and heat shock proteins (HSP) are activated in the event of heat stress and play a similar role here as chaperones to that of dehydrins in the event of cold and drought stress (Yu et al., 2005, Mol Cells 19: 328-333).

A number of plant-endogeneous signalling substances involved in stress tolerance or pathogen defence are already known. Examples here include salicylic acid, benzoic acid, jasmonic acid or ethylene [Biochemistry and Molecular Biology of Plants, pp. 850-929, American Society of Plant Physiologists, Rockville, Md., eds. Buchanan, Gruissem, Jones, 2000]. Some of these substances or the stable synthetic derivatives and derived structures thereof are also effective on external application to plants or in seed dressing, and activate defence reactions which cause elevated stress tolerance or pathogen tolerance of the plant [Sembdner, and Parthier, 1993, Ann. Rev. Plant Physiol. Plant Mol. Biol. 44: 569-589). The salicylate-mediated defence is directed in particular against phytopathogenic fungi, bacteria and viruses (Ryals et al., The Plant Cell 8, 1809-1819, 1996)

It is additionally known that chemical substances can increase the tolerance of plants to abiotic stress. Such substances are applied by seed dressing, by leaf spraying or by soil treatment. For instance, an increase in abiotic stress tolerance of crop plants by treatment with elicitors of systemic acquired resistance (SAR), abscisic acid derivatives or azibenzolar-S-methyl is described (Schading and Wei. WO-200028055, Abrams and Gusta, U.S. Pat. No. 5,201,931, Churchill et al., 1998, Plant Growth Regul 25: 35-45). Similar effects are also observed on application of fungicides, especially from the group of the strobilurins or of the succinate dehydrogenase inhibitors, and are frequently also accompanied by an increase in yield (Draber et al., DE-3534948, Bartlett et al., 2002, Pest Manag Sci 60: 309). It is likewise known that the herbicide glyphosate in low dosage stimulates the growth of some plant species (Cedergreen, Env. Pollution 2008, 156, 1099).

In addition, effects of growth regulators on the stress tolerance of crop plants have been described (Morrison and Andrews, 1992, J Plant Growth Regul 11: 113-117, RD-259027). In the event of osmotic stress, a protective effect has been observed as a result of application of osmolytes, for example glycine betaine or the biochemical precursors thereof, e.g. choline derivatives (Chen et al., 2000, Plant Cell Environ 23: 609-618, Bergmann et al., DE-4103253). The effect of antioxidants, for example naphthols and xanthines, to increase abiotic stress tolerance in plants has also already been described (Bergmann et al., DD-277832, Bergmann et al., DD-277835). However, the molecular causes of the anti-stress action of these substances are substantially unknown.

It is additionally known that the tolerance of plants to abiotic stress can be increased by a modification of the activity of endogamous poly-ADP-ribose polymerases (PARP) or poly-(ADP-ribose) glycohydrolases (PARG) (de Block et al., The Plant Journal, 2005, 41, 95; Levine et al., FEBS Lett. 1998, 440, 1; WO0004173; WO04090140).

It is thus known that plants possess several endogenous reaction mechanisms which can bring about effective defence against a wide variety of different harmful organisms and/or natural abiotic stress.

Since, however, the ecologic and economic demands on modern crop treatment compositions are increasing constantly, for example with respect to toxicity, selectivity, application rate, formation of residues and favourable manufacture, there is a constant need to develop novel crop treatment compositions which have advantages over those known, at least in some areas.

SUMMARY

Anthranilamide derivatives have already been described in WO 2007/144100. These documents also report an insecticidal action. Surprisingly, it has now been found that anthranilamide derivatives are highly suitable for controlling insects and/or spider mites and/or nematodes by drenching, soil mixing, furrow treatment, drip application, in hydroponic systems, by planting hole treatment, after dip application to roots, tuber or bulbs, using hydroponic systems or soil injection and also by stem or flower injection, dip application, floating or seedbox application or by treating seed.

It has also been found that, by using the anthranilamide derivatives, it is possible to enhance the stress tolerance of plants to abiotic stress, so that anthranilamide derivatives can be used in particular for enhancing plant growth and/or for increasing plant yield and/or for increasing the tolerance to drought and dry conditions.

DETAILED DESCRIPTION OF A PREFERRED EMBODIMENT

Accordingly, the present invention relates to the use of anthranilamide derivatives for controlling insects and/or spider mites and/or nematodes by drenching, mixing with the substrate, furrow treatment, in hydroponic and irrigations systems, as drip application, planting hole treatment or as dip application to, for example, roots, tuber or bulbs, or by soil, stem or flower injection, and for treating seed. The present invention furthermore relates to these application forms on natural substrates (soil) or artificial substrates (for example rockwool, glass wool, quartz sand, gravel, expanded clay, vermiculite), outdoors or in closed systems (for example greenhouses or under cloches) and in annual (for example field crops, vegetables, spices, ornamental plants) or perennial (for example citrus plants, fruit, tropical crops, spices, nuts, wine, conifers and ornamental plants) crops.

The present invention furthermore relates to the use of anthranilamide derivatives for increasing the tolerance to abiotic stress in plants. The crops to be protected which have only been described in general terms will be described in greater detail and specified hereinbelow. Thus, regarding the use, field crops are understood as meaning cereal crops, for example wheat, barley, rye, oats, triticale, but also maize, cotton, soybeans, millet and rice, but also oilseed rape (canola), potatoes, sugar cane, sugar beet and sunflowers.

Thus, as regards the use, vegetables are understood as meaning for example fruiting vegetables and inflorescences as vegetables, for example bell peppers, chillies, tomatoes, aubergines, cucumbers, pumpkins, courgettes, broad beans, climbing and dwarf beans, peas, artichokes;

but also leafy vegetables, for example head-forming lettuce, chicory, endives, various types of cress, of rocket, lamb's lettuce, iceberg lettuce, leeks, spinach, Swiss chard;

furthermore tuberous, root and stalk vegetables, for example celeriac, red beetroot, carrots, radishes, horseradish, salsify, asparagus, turnips, palm shoots, bamboo shoots, moreover allium vegetables, for example onions, leek, fennel, garlic;

furthermore *Brassica* vegetables such as cauliflower, broccoli, kohlrabi, red cabbage, white cabbage, curly kale, Savoy cabbage, Brussel sprouts, Chinese cabbage.

Regarding the use, perennial crops are understood as meaning citrus, such as, for example, oranges, grapefruits, tangerines, lemons, limes, Seville oranges, kumquats, satsumas;

but also pome fruit such as, for example, apples, pears and quinces, and stone fruit, such as, for example, peaches, nectarines, cherries, plums, quetsch, apricots;

furthermore grapevines, hops, olives, tea and tropical crops such as, for example, mangoes, papayas, figs, pineapples, dates, bananas, durians, kaki fruit, coconuts, cacao, coffee, avocados, lychees, maracujas, guavas, moreover almonds and nuts such as, for example, hazelnuts, walnuts, pistachios, cashew nuts, para nuts, pecan nuts, butternuts, chestnuts, hickory nuts, macadamia nuts, peanuts, moreover also soft fruit such as, for example, redcurrants, gooseberries, raspberries, blackberries, blueberries, strawberries, cranberries, including American cranberries, kiwi fruit.

Regarding the use, ornamental plants are understood as meaning annual and perennial plants, for example cut flowers such as, for example, roses, carnations, gerbera, lilies, marguerites, chrysanthemums, tulips, narcissi, anemones, poppy, amaryllis, dahlias, azaleas, mallows, but also for example bedding plants, pot plants and perennials such as, for example, roses, Tagetes, violas, geraniums, fuchsias, hibiscus, chrysanthemum, busy lizzie, cyclamen, African violet, sunflowers, begonias, furthermore for example bushes and conifers such as, for example, ficus, rhododendron, firs, spruces, pines, including umbrella pines, yews, juniper, oleander.

Regarding the use, spices are understood as meaning annual and perennial plants such as, for example, aniseed, chilli, capsicum, pepper, vanilla, marjoram, thyme, cloves, juniper berries, cinnamon, tarragon, coriander, saffron, ginger. The anthranilamides which can used according to the invention as insecticides and/or acaricides and/or nematicides are defined by the general formula (I)

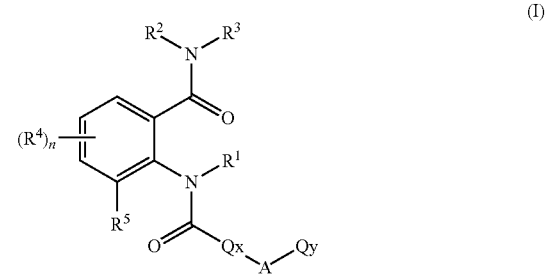

in which $R^1$ represents hydrogen, amino, hydroxyl or represents $C_1$-$C_6$-alkyl, $C_2$-$C_6$-alkenyl, $C_2$-$C_6$-alkynyl or $C_3$-$C_6$-cycloalkyl, each of which is optionally mono- or polysubstituted by identical or different substituents, where the substituents independently of one another may be selected from the group consisting of halogen, cyano, nitro, hydroxyl, $C_1$-$C_4$-alkoxy, $C_1$-$C_4$-alkylsulphonyl, ($C_1$-$C_4$-alkoxy)carbonyl, $C_1$-$C_4$-alkylamino, di-($C_1$-$C_4$-alkyl)amino, $C_3$-$C_6$-cycloalkylamino and ($C_1$-$C_4$-alkyl)-$C_3$-$C_6$-cycloalkylamino, R² represents hydrogen, C₁-C₆-alkyl, C₂-C₆-alkenyl, C₂-C₆-alkynyl, C₃-C₆-cycloalkyl, C₁-C₄-alkoxy, C₁-C₄-alkylamino, di-(C₁-C₄-alkyl)amino, C₃-C₆-cycloalkylamino, C₁-C₆-alkoxycarbonyl or C₁-C₆-alkylcarbonyl, R³ represents hydrogen or represents C₁-C₆-alkyl, C₁-C₆-alkoxy, C₂-C₆-alkenyl, C₂-C₆-alkynyl, C₃-C₆-cycloalkyl, C₃-C₁₂-cycloalkyl-C₁-C₆-alkyl, each of which is optionally mono- or polysubstituted by identical or different substituents, where the substituents independently of one another may be selected from the group consisting of amino, C₃-C₆-cycloalkylamino, halogen, cyano, carboxyl, carbamoyl, nitro, hydroxyl, C₁-C₆-alkyl, C₁-C₆-haloalkyl, C₃-C₆-cycloalkyl, C₁-C₄alkoxy, C₁-C₄-haloalkoxy, C₁-C₄-alkylthio, C₁-C₄-alkylsulphinyl, C₁-C₄-alkylsulphonyl, C₁-C₆-alkoxycarbonyl, C₁-C₆-alkylcarbonyl, C₃-C₆-trialkylsilyl and a saturated or partially saturated heterocyclic ring, an aromatic or heteroaromatic ring or a saturated, partially saturated or aromatic heterobicyclic ring, where the ring or the ring system is optionally mono- or polysubstituted by identical or different substituents from the group consisting of SF₅, halogen, cyano, nitro, hydroxyl, amino, carboxyl, carbamoyl, aminosulphonyl, C₁-C₆-alkyl, C₃-C₆-cycloalkyl, C₁-C₄-alkoxy, C₁-C₆-haloalkyl, C₁-C₄-haloalkoxy, C₁-C₄-alkylthio, C₁-C₄-alkylsulphonyl, C₁-C₄-alkylsulphinyl, C₁-C₄-alkylsulphimino, C₁-C₄-alkylsulphimino-C₁-C₄alkyl, C₁-C₄-alkylsulphimino-C₂-C₅-alkylcarbonyl, C₁-C₄alkylsulphoximino, C₁-C₄-alkylsulphoximino-C₁-C₄-alkyl, C₁-C₄alkylsulphoximino-C₂-C₅-alkylcarbonyl, C₂-C₆-alkoxycarbonyl, C₂-C₆-alkylcarbonyl, C₃-C₆-trialkylsilyl, benzyl C₂-C₆-alkenyl, C₂-C₆-alkynyl, C₂-C₆-haloalkenyl, C₂-C₆-haloalkynyl, C₃-C₆-halocycloalkyl, C₁-C₄-haloalkylthio, C₁-C₄-haloalkylsulphinyl, C₁-C₄-haloalkylsulphonyl, C₁-C₄-alkylamino, di-(C₁-C₄-alkyl)amino, C₃-C₆-cycloalkylamino, or a 3- to 6-membered ring, where the ring may optionally be substituted by C₁-C₆-alkyl, halogen, cyano, nitro, halo-(C₁-C₆)-alkyl, C₁-C₆-alkoxy or halo-(C₁-C₆)-alkoxy, or R³ represents C₁-C₆-alkoxycarbonyl, C₁-C₆-alkylcarbonyl, C₁-C₆-alkylaminocarbonyl or di-(C₁-C₆)alkylaminocarbonyl, or R³ furthermore represents a 5- or 6-membered aromatic or heteroaromatic ring, a 4-, 5- or 6-membered partially saturated ring or saturated heterocyclic ring, or a saturated, partially saturated or aromatic heterobicyclic ring which may optionally contain one to three heteroatoms from the group consisting of O, S and N, which rings are mono- or polysubstituted by identical or different substituents, where the substituents independently of one another are selected from the group consisting of SF₅, halogen, cyano, nitro, hydroxyl, amino, carboxyl, carbamoyl, C₁-C₆-alkyl, C₃-C₆-cycloalkyl, C₁-C₄-alkoxy, C₁-C₆-haloalkyl, C₁-C₄-haloalkoxy, C₁-C₄alkylthio, C₁-C₄-alkylsulphinyl, C₁-C₄-alkylsulphonyl, C₁-C₄-alkylsulphimino, C₁-C₄-alkylsulphimino-C₁-C₄-alkyl, C₁-C₄-alkylsulphimino-C₁-C₅-alkylcarbonyl, C₁-C₄-alkylsulphoximino, C₁-C₄-alkylsulphoximino-C₁-C₄-alkyl, C₁-C₄-alkylsulphoximino-C₂-C₅-alkylcarbonyl, C₁-C₆-alkoxycarbonyl, C₁-C₆-alkylcarbonyl, C₃-C₆-trialkylsilyl, C₂-C₆-alkenyl, C₂-C₆-alkynyl, C₂-C₆-haloalkenyl, C₂-C₆-haloalkynyl, C₃-C₆-halocycloalkyl, C₁-C₄-haloalkylthio, C₁-C₄-haloalkylsulphinyl, C₁-C₄-haloalkylsulphonyl, C₁-C₄-alkylamino, di-(C₁-C₄alkyl)amino and C₃-C₆-cycloalkylamino, or a 3- to 6-membered ring, where the ring may optionally be substituted by C₁-C₆-alkyl, halogen, cyano, nitro, halo-(C₁-C₆)-alkyl, C₁-C₆-alkoxy or halo-(C₁-C₆)-alkoxy, R² and R³ may be linked with each other via two to six carbon atoms and form a ring which optionally additionally contains a further nitrogen, sulphur or oxygen atom and which may optionally be mono- to tetrasubstituted by C₁-C₂-alkyl, C₁-C₂-haloalkyl, halogen, cyano, amino, C₁-C₂-alkoxy or C₁-C₂-haloalkoxy, R², R³ furthermore together represent =S(C₁-C₄-alkyl)₂ or =S(O)(C₁-C₄-alkyl)₂, R⁴ represents hydrogen, halogen, cyano, nitro C₁-C₄-alkyl, C₂-C₆-alkenyl, C₂-C₆-haloalkenyl, C₂-C₆-alkynyl, C₁-C₄alkoxy, C₁-C₄haloalkoxy, SF₅, C₁-C₄alkylthio, C₁-C₄-alkylstaphinyl, C₁-C₄-alkylsulphonyl, C₁-C₄haloalkylthio, C₁-C₄-haloalkylsulphinyl, C₁-C₄ haloalkylsulphonyl, C₁-C₄alkylamino, di-(C₁-C₄alkyl) amino, C₃-C₆-cycloalkylamino, (C₁-C₄-alkoxy)imino, (C₁-C₄alkyl)(C₁-C₄alkoxy)imino, (C₁-C₄haloalkyl)(C₁-C₄alkoxy)imino or C₃-C₆-trialkylsilyl, or two R⁴ via adjacent carbon atoms, form a ring which represents —(CH₂)₃—, —(CH₂)₄—, —(CH₂)₅—, —(CH=CH—)₂—, —OCH₂O—, —O(CH₂)₂O—, —OCF₂O—, —(CF₂)₂O—, —O(CF₂)₂O—, —(CH=CH—CH=N)— or —(CH=CH—N=CH)—, two R⁴ furthermore, via adjacent carbon atoms, form the fused rings below, which are optionally mono- or polysubstituted by identical or different substituents, where the substituents independently of one another may be selected from the group consisting of hydrogen, C₁-C₆-alkyl, C₃-C₆-cycloalkyl, C₁-C₆-haloalkyl, C₃-C₆-halocycloalkyl, halogen, C₁-C₆-alkoxy, C₁-C₄-alkylthio(C₁-C₆-alkyl), C₁-C₄-alkylsulphinyl(C₁-C₆-alkyl), C₁-C₄—alkylsulphonyl(C₁-C₆-alkyl), C₁-C₆-alkylamino, di-(C₁-C₄-alkyl)amino and C₃-C₆-cycloalkylamino,

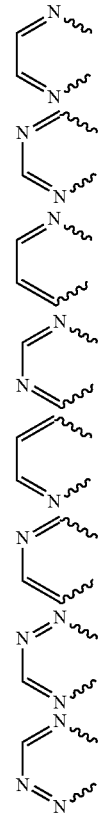

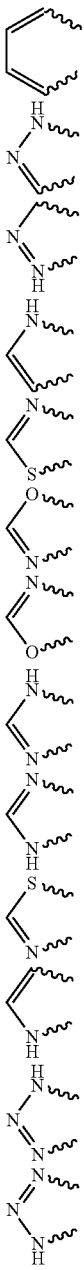

n represents 0 to 3,

R⁵ represents $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$haloalkylthio, $C_1$-$C_4$-haloalkylsulphinyl, $C_1$-$C_4$-haloalkylsulphonyl, halogen, cyano, nitro or $C_3$-$C_6$-trialkylsilyl, $Q_X$ represents an aromatic or heteroaromatic 5- or 6-membered ring which is optionally mono- or polysubstituted by identical or different substituents and which may contain 1-3 heteroatoms from the group consisting of N, S and O, A represents optionally mono- or polysubstituted —($C_1$-$C_6$-alkylene)-, —($C_2$-$C_6$-alkenylene)-, —($C_2$-$C_6$-alkynylene)-, —R⁸—($C_3$-$C_6$-cycloalkyl)-R⁸—, —R⁸—O—R⁸—, —R⁸—S—R⁸—, —R⁸—S(=O)—R⁸—, —R⁸—S(=O)₂—R⁸—, —R⁸—C₁-$C_6$-alkyl)-R⁸—, —R⁸—C=NO($C_1$-$C_6$-alkyl)-R⁸, —CH[CO₂($C_1$-$C_6$-alkyl)-, —R⁸—C(=O)—R⁸, —R⁸—C(=O)NH—R⁸, R⁸—C(=O)N($C_1$-$C_6$-alkyl)-R⁸, —R⁸—C(=O)NHNH—R⁸—, —R⁸—C(=O)N($C_1$-$C_6$-alkyl)-NH—R⁸—, —R⁸—C(=O)NHN($C_1$-$C_6$-alkyl)-R⁸, —R⁸—O (C=O)—R⁸, —R⁸—O (C=O)NH—R⁸, —R⁸—O (C=O)N($C_1$-$C_6$-alkyl)-R⁸, —R⁸—S(=O)₂NH—R⁸, —R⁸—S(=O)₂N($C_1$-$C_6$-alkyl)-R⁸, —R⁸—S(C=O)—R⁸, —R⁸—S(C=O)NH—R⁸, —R⁸—S(C=O)N($C_1$-$C_6$-alkyl)-R⁸, —R⁸—NHNH—R⁸, —R⁸—N($C_1$-$C_6$-alkyl)-NH—R⁸, —R⁸—N($C_1$-$C_6$-alkyl)-N($C_1$-$C_6$-alkyl)-R⁸, —R⁸—N=CH—O—R⁸, —R⁸—NH(C=O)O—R⁸, —R⁸—N($C_1$-$C_6$-alkyl)-(C=O)O—R⁸, —R⁸—NH(C=O)NH—R⁸, —R⁸—NH(C=S)NH—R⁸, —R⁸—NNS(=O)₂—R⁸, R⁸—NH—R⁸, R³—C(=O)—C(O)—R⁸, R⁸—C(OH)—R⁸, R⁸—NH(C=O)—R⁸, R⁸-Qz-R⁸, R⁸—C(=N—NR'₂)—R⁸, R⁸—C(=C—R'₂)—R⁸ or —R⁸—N($C_1$-$C_6$-alkyl)S(=O)₂—R⁸, where the substituents independently of one another may be selected from the group consisting of halogen, cyano, nitro, hydroxyl, $C_1$-$C_6$-alkyl, $C_1$-$C_6$-alkyloxy, halo-$C_1$-$C_6$-alkyl, amino, ($C_1$-$C_6$-alkyl)amino, di-($C_1$-$C_6$-alkyl)amino and $C_3$-$C_6$-cycloalkyl where —($C_3$-$C_6$-cycloalkyl)- in the ring may optionally contain 1 or 2 heteroatoms selected from the group consisting of N, S and O, R⁸ represents straight-chain or branched —($C_1$-$C_6$-alkylene)- or represents a direct bond, where a plurality of R⁸ independently of one another represent straight-chain or branched —($C_1$-$C_6$-alkylene)- or represent a direct bond, for example, R⁸—O—R⁸— represents —($C_1$-$C_6$-alkylene)-O—($C_1$-$C_6$-alkylene)-, —($C_1$-$C_6$-alkylene)-O—, —O—($C_1$-$C_6$-alkylene)-, or —O—, where R' represents alkyl, alkylcarbonyl, alkenyl, alkynyl, which may optionally be mono- or polysubstituted by halogen, Qz represents a 3- or 4-membered partially saturated or saturated or a 5- or 6-membered partially saturated, saturated or aromatic ring or represents a 6- to 10-membered bicyclic ring system, where the ring or the bicyclic ring system may optionally contain 1-3 heteroatoms from the group consisting of N, S and O, where the ring or the bicyclic ring system is optionally mono- or polysubstituted by identical or different substituents and where the substituents independently of one another may be selected from the group consisting of hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, carbamoyl, nitro, hydroxyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$haloalkylsulphonyl, di-($C_1$-$C_4$alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl and di-($C_1$-$C_4$alkyl)aminocarbonyl, $Q_Y$ represents a 5- or 6-membered partially saturated or saturated heterocyclic or heteroaromatic ring or an aromatic 8-, 9- or 10-membered fused heterobicyclic ring system, where the ring or the ring system is optionally mono- or polysubstituted by identical or different substituents and the substituents independently of one another may be selected from the group consisting of hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, carboxyl, carbamoyl, nitro, hydroxyl, $C_1$-$C_4$-alkoxy, $C_1$-$C_4$-haloalkoxy, $C_1$-$C_4$alkylthio, $C_1$-$C_4$alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, tri-($C_1$-$C_2$)alkylsilyl and ($C_1$-$C_4$-alkyl)($C_1$-$C_4$-alkoxy)imino, or where the substituents independently of one another may be selected from the group consisting of phenyl and a 5- or 6-membered heteroaromatic ring, where phenyl or the ring may optionally be mono- or polysubstituted by identical or different substituents from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, nitro, hydroxyl, $C_1$-$C_4$-alkoxy and $C_1$-$C_4$haloalkoxy, $R^7$ represents hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_1$-$C_6$-cycloalkoxy or

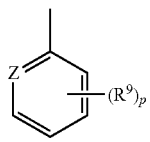

$R^9$ independently of one another represent hydrogen, $C_1$-$C_6$-alkyl, $C_3$-$C_6$-cycloalkyl, $C_1$-$C_6$-haloalkyl, halogen, cyano, nitro, $C_1$-$C_4$-alkoxy, $C_1$-$C_4$-haloalkoxy, $C_1$-$C_4$-alkylthio or $C_1$-$C_4$-haloalkylthio, p represents 0 to 4, Z represents N, CH, CF, CCl, CBr or Cl, the compounds of the general formula (I) further comprise N-oxides and salts.

For the use according to the invention, preference, particular preference, very particular preference or special preference is given to active compounds of the formula (I) where $R^1$ preferably represents hydrogen, $C_1$-$C_6$-alkyl, $C_2$-$C_6$-alkenyl, $C_2$-$C_6$-alkynyl, $C_3$-$C_6$-cycloalkyl, cyano($C_1$-$C_6$-alkyl), $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, $C_1$-$C_4$-alkylthio-$C_1$-$C_4$-alkyl, $C_1$-$C_4$-alkylsulphinyl-$C_1$-$C_4$-alkyl or $C_1$-$C_4$-alkylsulphonyl-$C_1$-$C_4$-alkyl, $R^1$ particularly preferably represents hydrogen, methyl, cyclopropyl, cyanomethyl, methoxymethyl, methylthiomethyl, methylsulphinylmethyl or methylsulphonylmethyl, $R^1$ very particularly preferably represents hydrogen, $R^2$ preferably represents hydrogen or $C_1$-$C_6$-alkyl.

$R^2$ particularly preferably represents hydrogen or methyl.

$R^2$ very particularly preferably represents hydrogen.

$R^3$ preferably represents hydrogen or represents $C_1$-$C_4$-alkyl, $C_1$-$C_4$-alkoxy, $C_2$-$C_4$-alkenyl, $C_2$-$C_4$-alkynyl, $C_3$-$C_6$-cycloalkyl, each of which is optionally mono- or polysubstituted by identical or different substituents, where the substituents independently of one another may be selected from the group consisting of halogen, cyano, carboxyl, carbamoyl, nitro, hydroxyl, $C_1$-$C_4$-alkyl. $C_1$-$C_4$-haloalkyl, $C_3$-$C_6$-cycloalkyl, $C_1$-$C_4$alkoxy, $C_1$-$C_4$haloalkoxy, $C_1$-$C_4$alkylthio, $C_1$-$C_4$-alkylsulphonyl, $C_1$-$C_4$-alkoxycarbonyl, $C_1$-$C_4$-alkylcarbonyl or a phenyl ring or a 4-, 5- or 6-membered aromatic, partially saturated or saturated heterocyclic ring, where the phenyl ring or heterocyclic ring is optionally mono- or polysubstituted by identical or different substituents and where the substituents independently of one another may be selected from the group consisting of hydrogen. $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, carboxyl, carbamoyl, $NO_2$, hydroxyl, $C_1$-$C_4$-alkoxy, $C_1$-$C_4$haloalkoxy, $C_1$-$C_4$-alkylthio, $C_1$-$C_4$-alkylsulphinyl, $C_1$-$C_4$-alkylsulphonyl, $C_1$-$C_4$haloalkylthio, $C_1$-$C_4$-haloalkylsulphinyl, $C_1$-$C_4$-haloalkylsulphonyl, $C_1$-$C_4$-alkylamino, di-($C_1$-$C_4$alkyl)amino, $C_3$-$C_6$-cycloalkylamino, ($C_1$-$C_6$-alkyl)carbonyl, ($C_1$-$C_6$-alkoxy)carbonyl or $R^3$ preferably represents $C_2$-$C_4$-alkoxycarbonyl, $C_2$-$C_4$-alkylcarbonyl, $C_2$-$C_4$-alkylaminocarbonyl or $C_2$-$C_4$-dialkylaminocarbonyl, or $R^3$ preferably represents a phenyl ring, a 5- or 6-membered aromatic heterocyclic ring or a 4-, 5- or 6-membered partially saturated or saturated heterocyclic ring which may contain 1-3 heteroatoms from the group consisting of N, S and O, where the phenyl ring or heterocyclic ring is optionally mono- or polysubstituted by identical or different substituents, and where the substituents independently of one another may be selected from the group consisting of hydrogen. $C_1$-$C_4$-alkyl, $C_2$-$C_4$-alkenyl, $C_2$-$C_4$-alkynyl, $C_3$-$C_6$-cycloalkyl, $C_1$-$C_4$-haloalkyl, $C_2$-$C_4$-haloalkenyl, $C_2$-$C_4$-haloalkynyl, $C_3$-$C_6$-halocycloalkyl, halogen, cyano, carboxyl, carbamoyl, $NO_2$, hydroxyl, $C_1$-$C_4$-alkoxy, $C_1$-$C_4$-haloalkoxy, $C_1$-$C_4$ alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, $C_3$-$C_6$-cycloalkylamino, ($C_1$-$C_4$-alkyl)carbonyl and ($C_1$-$C_4$-alkoxy)carbonyl, $R^3$ particularly preferably represents hydrogen or represents $C_1$-$C_4$-alkyl or $C_3$-$C_6$-cycloalkyl, each of which is optionally mono- or polysubstituted by identical or different substituents, where the substituents independently of one another may be selected from the group consisting of halogen, cyano, carboxyl, hydroxyl. $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_2$-$C_4$-alkoxycarbonyl, $C_2$-$C_6$-alkylcarbonyl and a phenyl ring and a 4-, 5- or 6-membered aromatic, partially saturated or saturated heterocyclic ring, where the phenyl ring or heterocyclic ring is optionally mono- or polysubstituted by identical or different substituents, and where the substituents independently of one another may be selected from the group consisting of hydrogen, $C_1$-$C_4$-alkyl, $C_3$-$C_6$-cycloalkyl, $C_1$-$C_4$-haloalkyl, $C_2$-$C_4$-haloalkenyl, $C_2$-$C_4$-haloalkynyl, $C_3$-$C_6$-halocycloalkyl, halogen, cyano, hydroxyl, $C_1$-$C_4$-alkoxy and $C_1$-$C_4$-haloalkoxy, or $R^3$ particularly preferably represents $C_2$-$C_4$-alkoxycarbonyl, $C_2$-$C_4$-alkylcarbonyl or $C_2$-$C_4$-alkylaminocarbonyl, or $R^3$ particularly preferably represents a phenyl ring, a 5- or 6-membered aromatic heterocyclic ring or a 4-, 5- or 6-membered partially saturated or saturated heterocyclic ring which may contain 1-3 heteroatoms from the group consisting of N, S and O, where the phenyl ring or heterocyclic ring is optionally mono- or polysubstituted by identical or different substituents, and where the substituents independently of one another may be selected from the group consisting of hydrogen, $C_1$-$C_4$-alkyl, $C_2$-$C_4$-alkenyl, $C_2$-$C_4$-alkynyl, $C_3$-$C_6$-cycloalkyl, $C_1$-$C_4$-haloalkyl, $C_2$-$C_4$-haloalkenyl, $C_2$-$C_4$-haloalkynyl, $C_3$-$C_6$-halocycloalkyl, halogen, cyano, carbamoyl, $NO_2$, hydroxyl, $C_1$-$C_4$-alkoxy and $C_1$-$C_4$-haloalkoxy, or R³ very particularly preferably represents hydrogen, methyl, ethyl, n-propyl, isopropyl, n-butyl, isobutyl, sec-butyl, ten-butyl, cyclopropyl, cyclobutyl, azetidine, oxetane, thietane, pyrrolidine, pyrazolidine, imidazolidine, imidazolidinone, tetrahydrofuran, tetrahydrothiophene, tetrahydrothiophene dioxide, thiazoline, thiazolidine, piperidine, piperazine, tetrahydropyran, dihydrofuranone, dioxane, morpholine, thiomorpholine, thiomorpholine dioxide, phenyl or pyridyl, or R³ especially preferably represents hydrogen, methyl, isopropyl, cyclopropyl or tert-butyl.

R⁴ preferably represents hydrogen, $C_1$-$C_4$-alkyl, $C_1$-$C_4$haloalkyl, halogen, cyano, $C_1$-$C_4$-alkoxy, $C_1$-$C_4$-haloalkoxy, $C_1$-$C_4$-alkylthio or $C_1$-$C_4$haloalkylthio, two adjacent radicals R⁴ likewise preferably represent —(CH$_2$)$_3$—, —(CH$_2$)$_4$—, —(CH$_2$)$_5$—, —(CH═CH—)$_2$—, —OCH$_2$O—, —O(CH$_2$)$_2$O—, —OCF$_2$O—, —(CF$_2$)$_2$O—, —O(CF$_2$)$_2$O—, —(CH═CH—CH═N)— or —(CH═CH—N═CH)—, R⁴ particularly preferably represents hydrogen, $C_1$-$C_4$-alkyl, $C_1$-$C_2$-haloalkyl, halogen, cyano or $C_1$-$C_2$-haloalkoxy, two adjacent radicals R⁴ particularly preferably represent —(CH$_2$)$_4$—, —(CH═CH—)$_2$, —O(CH$_2$)$_2$O—, —O(CF$_2$)$_2$O—, —(CH═CH—CH═N)— or —(CH═CH—N═CH)—, R⁴ very particularly preferably represents hydrogen, methyl, trifluoromethyl, cyano, fluorine, chlorine, bromine, iodine or trifluoromethoxy. Moreover, two adjacent radicals R⁴, very particularly preferably represent —(CH$_2$)$_4$— or —(CH═CH—)$_2$—.

R⁴ especially preferably represents chlorine, fluorine or bromine,

R⁴ furthermore especially preferably represents iodine or cyano.

Two adjacent radicals R⁴ especially preferably represent —(CH═CH—)$_2$ n preferably represents 0, 1 or 2, n particularly preferably represents 1 or 2, n very particularly preferably represents 1, R⁵ preferably represents $C_1$-$C_4$-alkyl, $C_3$-$C_6$-cycloalkyl, $C_1$-$C_4$-haloalkyl; $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$ haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl, R⁵ particularly preferably represents $C_1$-$C_4$-alkyl, $C_3$-$C_6$-cycloalkyl, $C_1$-$C_4$-haloalkyl, $C_1$-$C_6$-halocycloalkyl, $C_1$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, fluorine, chlorine, bromine, iodine, cyano, nitro or $C_3$-$C_6$-trialkylsilyl, R⁵ very particularly preferably represents methyl, fluorine, chlorine, bromine or iodine, R⁵ especially preferably represents methyl or chlorine, Qx preferably represents a 5- or 6-membered heteroaromatic ring which is optionally mono- or polysubstituted by identical or different R⁷ and which may contain 1-3 heteroatoms from the group consisting of N, O and S, or represents phenyl.

Qx particularly preferably represents a 5- or 6-membered ring selected from the group consisting of furan, thiophene, triazole, imidazole, thiazole, oxazole, isoxazole, isothiazole, thiadiazole, oxadiazole, pyrrole, pyridine, pyrimidine, pyridazine, pyrazine, phenyl or pyrazole, which ring is optionally mono- or polysubstituted by identical or different R⁷, Qx very particularly preferably represents thiazole, oxazole, pyrrole, imidazole, triazole, pyrimidine, phenyl or represents pyrazole which is monosubstituted by the group R⁷,

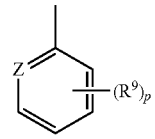

where Z, R and p may have the general definitions given above or the preferred or particularly preferred definitions given below, A preferably represents optionally mono- or polysubstituted -(C1-C4-alkylene)-, -(C2-C4-alkenylene)-, —(C$_2$-C$_4$-alkynylene)-, —R⁸—(C$_3$-C$_6$-cycloalkyl)-R⁸—, —R⁸—O—R⁸—, —R⁸—S—R⁸—, —R⁸—S(═O)—R⁸—, —R⁸—S(═O)$_2$—R⁸—, —R⁸—NH—(C$_1$-C$_4$-alkyl), —R⁸—N(C$_1$-C$_4$-alkyl)-R⁸, —R⁸—C═NO(C$_1$-C$_4$alkyl), —R⁸—C(═O)—R⁸, —R⁸—C(═S)—R⁸, —R⁸—C(═O)NH—R⁸, R⁸—C(═O)N(C$_1$-C$_4$-alkyl)-R⁸, —R⁸—S(═O)$_2$NH—R⁸, —R⁸—S(═O)$_2$N(C$_1$-C$_4$-alkyl)-R⁸, —R⁸—NH(C═O)O—R⁸, —R⁸—N(C$_1$-C$_4$-alkyl)-(C═O)O—R⁸, —R⁸—NH(C═O)NH—R⁸, —R⁸—NHS(═O)$_2$—R⁸, —R⁸—N(C$_1$-C$_4$-alkyl)S(═O)$_2$—R⁸, R⁸—NH—R⁸, R⁸—C(═O)—C(═O)—R⁸, R⁸—C(OH)—R⁸ or R⁸-Qz-R⁸, where the substituents independently of one another may be selected from the group consisting of halogen, cyano, nitro, hydroxyl, $C_1$-$C_6$-alkyl, $C_1$-$C_6$-alkoxy and halo-$C_1$-$C_6$-alkyl, where Qz may have the general definitions given above or the preferred or particularly preferred definitions given below, A particularly preferably represents —CH$_2$—, —CH$_2$O—, —CH$_2$OCH$_2$—, —CH$_2$S—, —CH$_2$SCH$_2$—, —CH$_2$N(C$_1$-C$_6$alkyl)-, —CH$_2$N(C$_1$-C$_4$-alkyl)CH$_2$—, —CH(Hal)-, —C(Hal)$_2$-, —CH(CN)—, CH$_2$(CO)—, CH$_2$(CS)—, CH$_2$CH(OH)—, -cyclopropyl-, CH$_2$(CO)CH$_2$—, —CH(C$_1$-C$_4$-Alkyl)-, —C(di-C$_1$-C$_6$-alkyl)-, —CH$_2$CH$_2$—, —CH═CH—, —C≡C—, —C═NO(C$_1$-C$_6$-alkyl) or —C(═O)(C$_1$-C$_4$-alkyl), A very particularly preferably represents —CH$_2$—, —CH(CH$_3$), C(CH$_3$)$_2$, —CH$_2$CH$_2$—, —CH(CN)—, —CH$_2$O— or —C(═O)—CH$_2$—, A especially preferably represents CH$_2$, CH(CH$_3$), —CH$_2$O— or —C(═O)—CH$_2$—.

Qz preferably represents a 3- or 4-membered partially saturated or saturated or a 5- or 6-membered partially saturated, saturated or aromatic ring, where the ring may optionally contain 1-3 heteroatoms from the group consisting of N, S and O, where the ring is optionally mono- or polysubstituted by identical or different substituents, and where the substituents independently of one another may be selected from the group consisting of hydrogen, $C_1$-$C_6$-alkenyl, $C_2$-$C_6$-alkynyl, $C_3$-$C_5$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, hydroxyl, $C_1$-$C_4$alkoxy, $C_1$-$C_4$haloalkoxy, $C_1$-$C_4$-alkylthio, $C_1$-$C_4$alkylsulphinyl, $C_1$-$C_4$-alkylsulphonyl, $C_1$-$C_4$-haloalkylthio, $C_1$-$C_4$haloalkylsulphinyl and $C_1$-$C_4$-haloalkylsulphonyl, Qz particularly preferably represents a 3- or 4-membered partially saturated or saturated or a 5-membered partially saturated, saturated or aromatic ring, where the ring may optionally contain 1-2 heteroatoms from the group consisting of N, S and O, where the ring is optionally mono- or polysubstituted by identical or different substituents, and where the substituents independently of one another may be selected from the group consisting of hydrogen, $C_1$-$C_6$-alkyl, $C_2$-$C_6$-alkenyl, $C_2$-$C_6$-alkynyl, $C_3$-$C_6$cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, hydroxyl, $C_1$-$C_4$-alkoxy, $C_1$-$C_4$-haloalkoxy, $C_1$-$C_4$-alkylthio, $C_1$-$C_4$-alkylsulphonyl, $C_1$-$C_4$haloalkylthio, $C_1$-$C_4$haloalkylsulphinyl and $C_1$-$C_4$haloalkylsulphonyl, Qz very particularly preferably represents azetidine, oxetane or thietane, pyrrolidine, pyrroline, pyrazolidine, pyrazoline, imidazolidine, imidazolidone, imidazoline, tetrahydrofuran, tetrahydrothiophene, thiazolidine, isothiazolidine or isoxazoline, which is optionally mono- or polysubstituted by identical or different substituents, and where the substituents independently of one another may be selected from the group consisting of hydrogen, methyl, ethyl, isopropyl, hydroxyl, methoxy, trifluoromethoxy, fluorine, chlorine, bromine, cyano, difluoromethyl, tri fluoromethyl, $R^7$ preferably represents $C_1$-$C_6$-alkyl or represents the radical

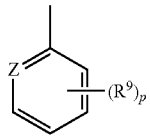

$R^7$ furthermore preferably represents $C_3$-$C_6$-cycloalkoxy,
$R^7$ particularly preferably represents methyl or represents the radical

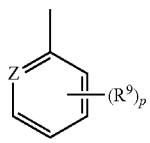

$R^9$ independently of one another preferably represent hydrogen, halogen, cyano, $C_1$-$C_4$-alkyl, $C_1$-$C_4$-alkoxy, $C_1$-$C_4$-haloalkyl, $C_1$-$C_4$-haloalkoxy, $C_1$-$C_4$haloalkylsulphonyl or ($C_1$-$C_4$-alkyl)-$C_1$-$C_4$-alkoxyimino,
$R^9$ independently of one another particularly preferably represent hydrogen, halogen, cyano or $C_1$-$C_4$-haloalkyl,
$R^9$ independently of one another very particularly preferably represent fluorine, chlorine or bromine,
$R^9$ especially preferably represents chlorine.
p preferably represents 1, 2 or 3,
p particularly preferably represents 1 or 2,
p very particularly preferably represents 1,
Z preferably represents N, CH, CF, CCl, CBr or Cl,
Z particularly preferably represents N, CH, CF, CCl or CBr,
Z very particularly preferably represents N, CCl or CH,
$R^8$ preferably represents straight-chain or branched —($C_1$-$C_4$alkylene)- or represents a direct bond.
$R^8$ particularly preferably represents methyl, ethyl, propyl, isopropyl, n-butyl, sec-butyl or isobutyl or a direct bond,
$R^8$ very particularly preferably represents methyl or ethyl or a direct bond,
Qy preferably represents a 5- or 6-membered partially saturated or saturated heterocyclic or heteroaromatic ring or an aromatic 8-, 9- or 10-membered fused heterobicyclic ring system, where the heteroatoms may be selected from the group consisting of N, S and O, where the ring or the ring system is optionally mono- or polysubstituted by identical or different substituents, and where the substituents independently of one another may be selected from the group consisting of hydrogen, $C_1$-$C_6$-alkyl, $C_2$-$C_6$-alkenyl, $C_2$-$C_6$-alkynyl, $C_1$-$C_6$-cycloalkyl, $C_2$-$C_6$-haloalkenyl, $C_2$-$C_6$-haloalkynyl, $C_3$-$C_6$-halocycloalkyl, halogen, cyano, carboxyl, carbamoyl, nitro, hydroxyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$haloalkylsulphinyl, $C_1$-$C_4$-haloalkylsulphonyl, or where the substituents independently of one another may be selected from the group consisting of phenyl and a 5- or 6-membered heteroaromatic ring, where phenyl or the ring may optionally be mono- or polysubstituted by identical or different substituents from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, nitro, hydroxyl, $C_1$-$C_4$-alkoxy and $C_1$-$C_4$-haloalkoxy, Qy particularly preferably represents an optionally mono- or polysubstituted 5- or 6-membered heteroaromatic ring from the group consisting of Q-1 to Q-53 and Q-58 to Q-59, Q62 to Q63, an aromatic 9-membered fused heterobicyclic ring system Q-54 to Q-56 or a 5-membered heterocyclic ring Q-60 to Q-61, where the substituents independently of one another may be selected from the group consisting of $C_1$-$C_3$-alkyl, $C_1$-$C_3$-haloalkyl, $C_1$-$C_2$-alkoxy, halogen, cyano, hydroxyl, nitro or $C_1$-$C_2$-haloalkoxy, or where the substituents independently of one another may be selected from the group consisting of phenyl and a 5- or 6-membered heteroaromatic ring, where phenyl or the ring may optionally be mono- or polysubstituted by identical or different substituents from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, $NO_2$, hydroxyl, $C_1$-$C_4$-alkoxy and $C_1$-$C_4$-haloalkoxy, Qy very particularly preferably represents an optionally mono- or polysubstituted 5- or 6-membered heteroaromatic ring from the group consisting of Q-36 to Q-40, Q43, Q-58 to Q-59, Q62, Q63, an aromatic 9-membered fused heterobicyclic ring system Q-54 to Q-56 or a 5-membered heterocyclic ring Q-60 to Q-61, where the substituents independently of one another may be selected from the group consisting of $C_1$-$C_3$-alkyl, $C_1$-$C_3$-haloalkyl, $C_1$-$C_2$-alkoxy, halogen, cyano, hydroxyl, nitro or $C_1$-$C_{27}$haloalkoxy, or where the substituents independently of one another may be selected from the group consisting of phenyl and a 5- or 6-membered heteroaromatic ring, where phenyl or the ring may optionally be mono- or polysubstituted by identical or different substituents from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, nitro, $C_1$-$C_4$-alkoxy and $C_1$-$C_4$-haloalkoxy, Qy especially preferably represents a heteroaromatic ring from the group consisting of Q-37, Q-38, Q-39, Q-40, Q43, Q-58, Q-59, Q62 and Q63 which is optionally mono- or polysubstituted by identical or different substituents, or represents a 5-membered heterocyclic ring Q-60, where the substituents independently of one another may be selected from the group consisting of methyl, ethyl, cyclopropyl, tert-butyl, chlorine, fluorine, iodine, bromo, cyano, nitro, difluoromethyl, trifluoromethyl, pentafluoroethyl, n-heptafluoropropyl and isoheptafluoropropyl or the substituents being selectable independently of one another from phenyl or a 5- or 6-membered heteroaromatic ring, the substituents being selectable independently of one another from methyl, ethyl, cyclopropyl, tort-butyl, chloro, fluoro, iodo, bromo, cyano, nitro, difluoromethyl, trifluoromethyl, pentafluorethyl, n-heptafluoropropyl and isoheptafluoropropyl.

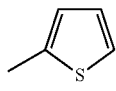
Q-1

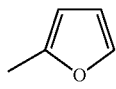
Q-2

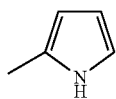
Q-3

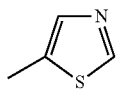
Q-4

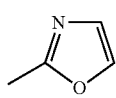
Q-5

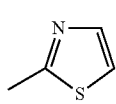
Q-6

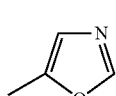
Q-7

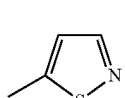
Q-8

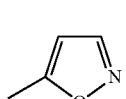
Q-9

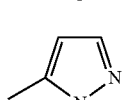
Q-10

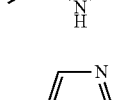
Q-11

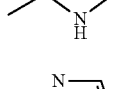
Q-12

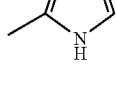
Q-13

-continued

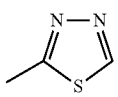
Q-14

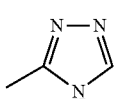
Q-15

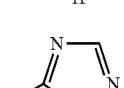
Q-16

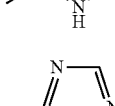
Q-17

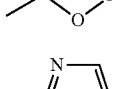
Q-18

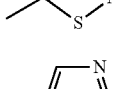
Q-19

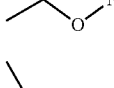
Q-20

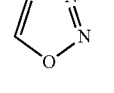
Q-21

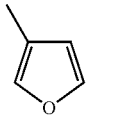
Q-22

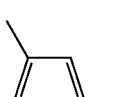
Q-23

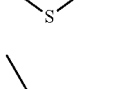
Q-24

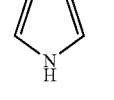
Q-25

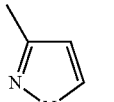
Q-26

-continued
Q-27 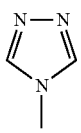
Q-28 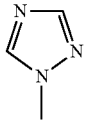
Q-29 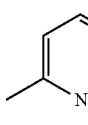
Q-30 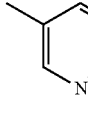
Q-31 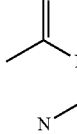
Q-32 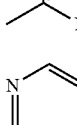
Q-33 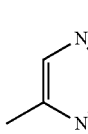
Q-34 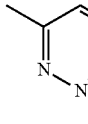
Q-35 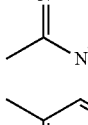
Q-36 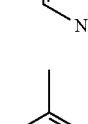
Q-37 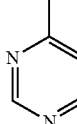
Q-38 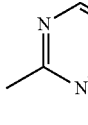
-continued
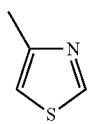
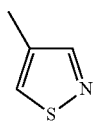
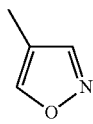
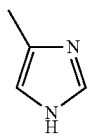
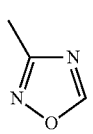
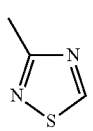
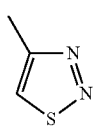
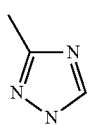
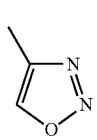
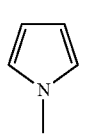
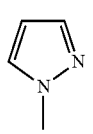
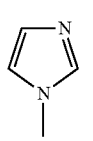
Q-39
Q-40
Q-41
Q-42
Q-43
Q-44
Q-45
Q-46
Q-47
Q-48
Q-49
Q-50
Q-51

-continued

Q-52 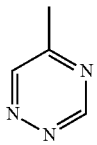

Q-53 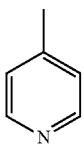

Q-54 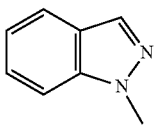

Q-55 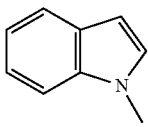

Q-56 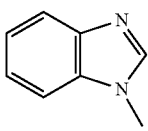

Q-57 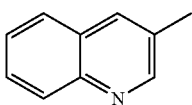

Q-58 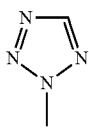

Q-59 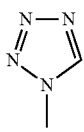

Q-60 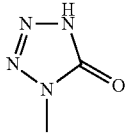

-continued

Q-61 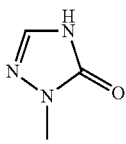

Q-62 

Q-63 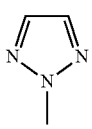

Independently of one another, the rings or ring systems listed above may additionally be substituted by oxo, thioxo, (=O)=NH, (=O)=N—CN, (=O)₂. Tetrahydrothiophene dioxide and imidazolidone may be mentioned by way of example.

In this case, the oxo group as substituent at a ring carbon atom, for example, is a carbonyl group in the heterocyclic ring. As a result, lactones and lactams are preferably also included. The oxo group may also be present at the hetero ring atomes which can occur in various oxidation states, for example at N and S, in which case they form, for example, the divalent groups —N(O)—, —S(O)— (also abbreviated as SO) and —S(O)₂— (also abbreviated as SO₂) in the heterocyclic ring. In the case of —N(O)— and —S(O)— groups, in each case both enantiomers are included.

At a heterocyclic ring, substituents other than the oxo group may also be attached to a heteroatom, for example at a nitrogen atom, if during the process a hydrogen atom at the nitrogen atom of the parent structure is replaced. In the case of the nitrogen atom and also other heteroatoms such as, for example, the sulphur atom, further substitution with formation of quaternary ammonium compounds or sulphonium compounds is also possible.

In particular, the compounds of the formula (I) can be present in the form of various regioisomers. For example in the form of mixtures of compounds having the definition Q62 or Q63 or in the form of mixtures of Q58 and Q59. Accordingly, the invention also embraces active compound combinations comprising mixtures of compounds of the formula (I) where Qy has the meanings Q62 and Q63, and also Q58 and Q59, and the compounds may be present in various mixing ratios, and one or more active compounds from group (II). Preference is given here to mixing ratios of compounds of the formula (I) in which the radical Qy represents Q62 or Q58 to compounds of the formula (I) in which the radical Qy represents Q63 or Q59 of from 60:40 to 99:1, particularly preferably from 70:30 to 97:3, very particularly preferably from 80:20 to 95:5. Special preference is given to the following mixing ratios of a compound of the formula (I) where Qy has the meaning Q62 or Q58 to a compound of the formula (I) where Qy has the meaning Q63 or Q59: 80:20; 81:19; 82:18; 83:17; 84:16; 85:15, 86:14; 87:13; 88:12: 89:11; 90:10, 91:9; 92:8; 93:7; 96:6; 95:5.

For the use according to the invention, preference is furthermore given to active compounds of the formula (I-1)

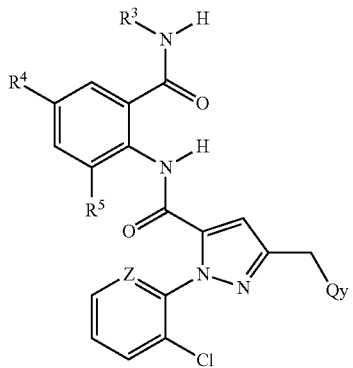

(I-1)

in which
R³ represents hydrogen or represents $C_1$-$C_6$-alkyl, $C_1$-$C_6$-alkoxy, $C_2$-$C_6$-alkenyl, $C_2$-$C_6$-alkynyl, $C_3$-$C_{12}$-cycloalkyl, $C_3$-$C_{12}$-cycloalkyl-$C_1$-$C_6$-alkyl, each of which is optionally mono- or polysubstituted by identical or different substituents, where the substituents independently of one another may be selected from the group consisting of halogen, amino, cyano, nitro, hydroxyl, $C_1$-$C_6$-alkyl, $C_3$-$C_6$-cycloalkyl, $C_1$-$C_4$alkoxy, $C_1$-$C_4$-haloalkoxy, $C_1$-$C_4$-alkylthio, $C_2$-$C_6$-alkoxycarbonyl, $C_1$-$C_6$-alkylcarbonyl $C_1$-$C_6$-cycloalkylamino and a 5- or 6-membered heteroaromatic ring, R⁴ represents halogen, cyano or methyl, R⁵ represents methyl or chlorine, Z represents N, CCl or CH, Qy represents an optionally mono- or polysubstituted 5- or 6-membered heteroaromatic ring from the group consisting of Q-36 to Q-40, Q43, Q-58 to Q-59, Q62, Q63, an aromatic 9-membered fused heterobicyclic ring system Q-54 to Q-56 or a 5-membered heterocyclic ring Q-60 to Q-61, where the substituents independently of one another may be selected from the group consisting of $C_1$-$C_3$-alkyl, $C_1$-$C_3$-haloalkyl, $C_1$-$C_2$-alkoxy, halogen, cyano, hydroxyl, nitro or $C_1$-$C_2$-haloalkoxy, where the compounds of the formula (I-1) may be present in the form of salts.

For the use according to the invention, preference, particular preference, very particular preference or special preference is given to active compounds of the formula (I-1) where R³ preferably represents hydrogen or represents $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, each of which is optionally mono- or polysubstituted by identical or different substituents, where the substituents independently of one another may be selected from the group consisting of halogen, cyano, amino, hydroxyl, $C_1$-$C_6$-alkyl, $C_1$-$C_4$alkoxy, $C_1$-$C_4$-haloalkoxy, $C_1$-$C_4$-alkylthio, $C_3$-$C_6$-cycloalkyl and a 5- or 6-membered heteroaromatic ring which contains 1-2 heteroatoms from the group consisting of N, O and S, where two oxygen atoms in the ring are not adjacent, R³ particularly preferably represents one of the radicals below

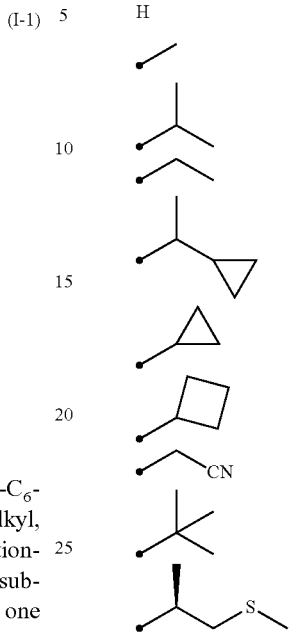

R⁴ preferably represents halogen, cyano or methyl,
R⁴ particularly preferably represents chlorine or cyano,
R⁴ also particularly preferably represents bromine, fluorine, iodine or methyl.
R⁵ preferably and particularly preferably represents methyl,
Z preferably represents N or CH,
Qy preferably represents a heteroaromatic ring from the group consisting of Q-37, Q-38, Q-39, Q-40, Q43, Q-58, Q-59, Q62 and Q63 which is optionally mono- or polysubstituted by identical or different substituents, or represents a 5-membered heterocyclic ring Q-60, where the substituents independently of one another may be selected from the group consisting of methyl, ethyl, cyclopropyl, tert-butyl, chlorine, fluorine, iodine, bromo, cyano, nitro, difluoromethyl, trifluoromethyl, pentafluoroethyl, n-heptafluoropropyl and isoheptafluoropropyl.
Qy particularly preferably represents a heteroaromatic ring from the group consisting of Q-58 and Q-59 which is optionally mono- or polysubstituted by identical or different substituents, where the substituents independently of one another may be selected from the group consisting of methyl, ethyl, cyclopropyl, tert-butyl, difluoromethyl, trifluoromethyl, pentafluoroethyl, n-heptafluoropropyl and isoheptafluoropropyl.

In particular, the compounds of the formula (I-1) can be present in the form of various regioisomers. For example in the form of mixtures of compounds having the definition Q62 or Q63 or in the form of mixtures of Q58 and Q59. Accordingly, the invention also embraces active compound combinations comprising mixtures of compounds of the formula (I-1) where Qy has the meanings Q62 and Q63, and also Q58 and Q59, and the compounds may be present in various mixing ratios, and one or more active compounds from group (II). Preference is given here to mixing ratios of compounds of the formula (I) in which the radical Qy represents Q62 or Q58 to compounds of the formula (I) in which the radical Qy represents Q63 or Q59 of from 60:40 to 99:1, particularly preferably from 70:30 to 97:3, very particularly preferably from 80:20 to 95:5. Special preference is given to the following mixing ratios of a compound of the formula (I) where Qy has the meaning Q62 or Q58 to a compound of the formula (I) where Qy has the meaning Q63 or Q59: 80:20; 81:19; 82:18; 83:17; 84:16; 85:15, 86:14; 87:13; 88:12; 89:11; 90:10, 91:9; 92:8; 93:7; 96:6; 95:5.
For the use according to the invention, particular preference is given to the active compounds of the formulae (I-1-1) to (I-1-71) below
(I-1-1)
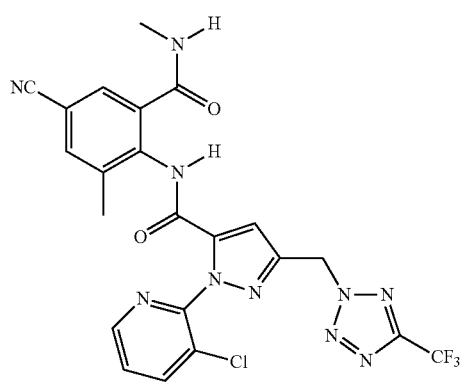
(I-1-2)
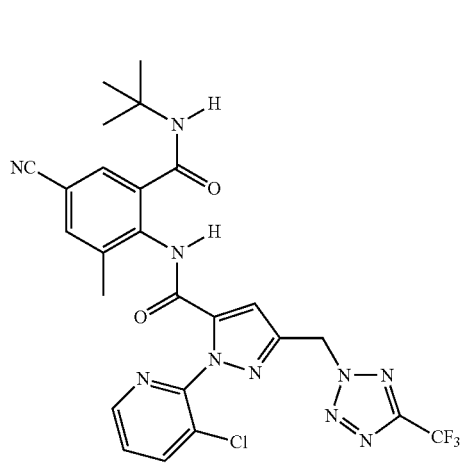
(I-1-3)
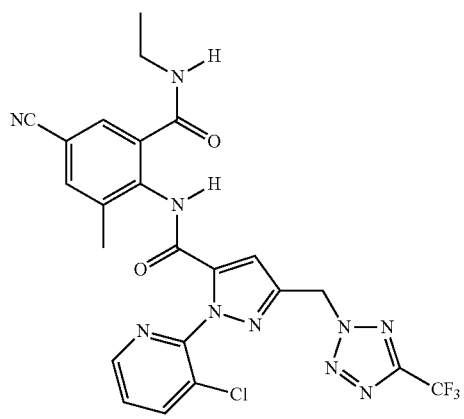
(I-1-4)
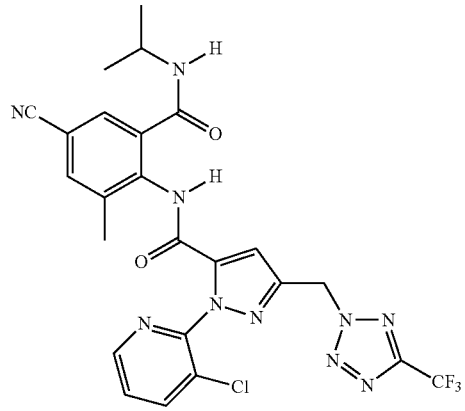
(I-1-5)
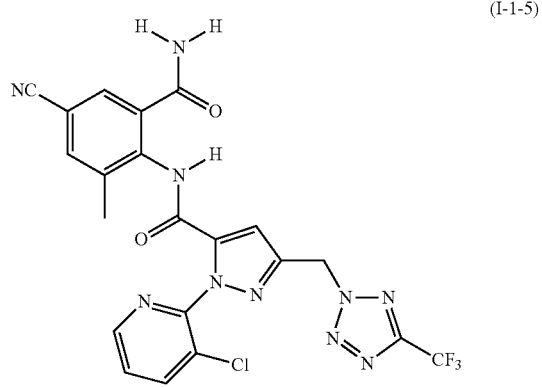
(I-1-6)
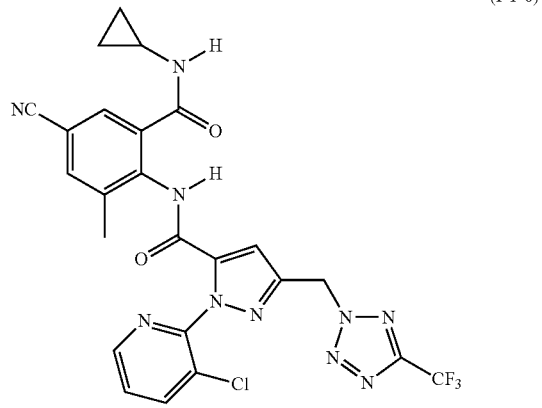
(I-1-7)
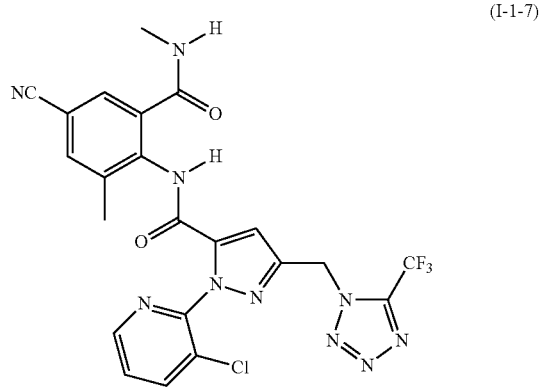

-continued
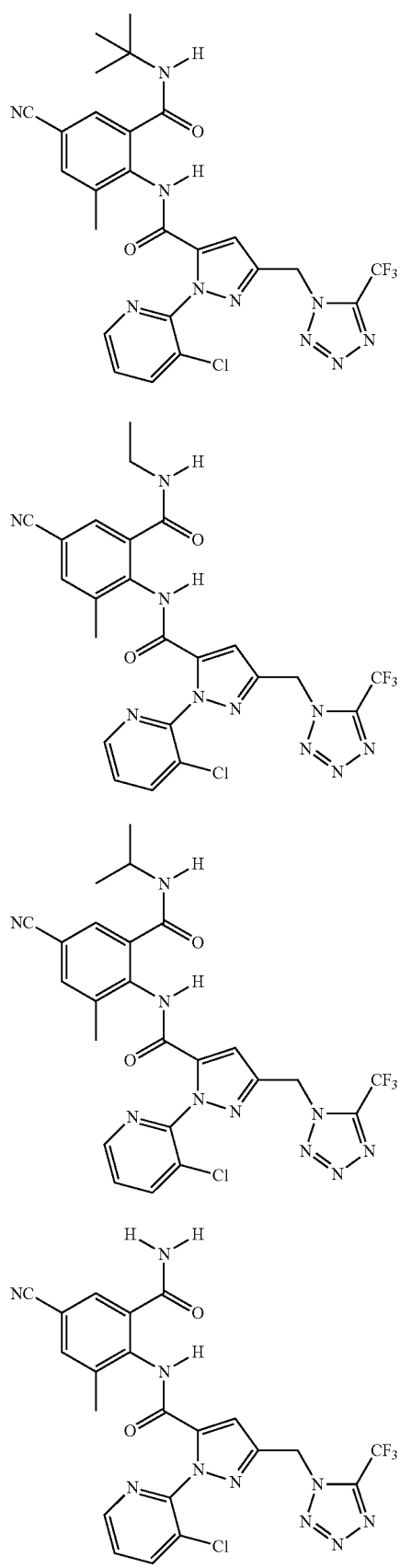
(I-1-8)
(I-1-9)
(I-1-10)
(I-1-11)
-continued
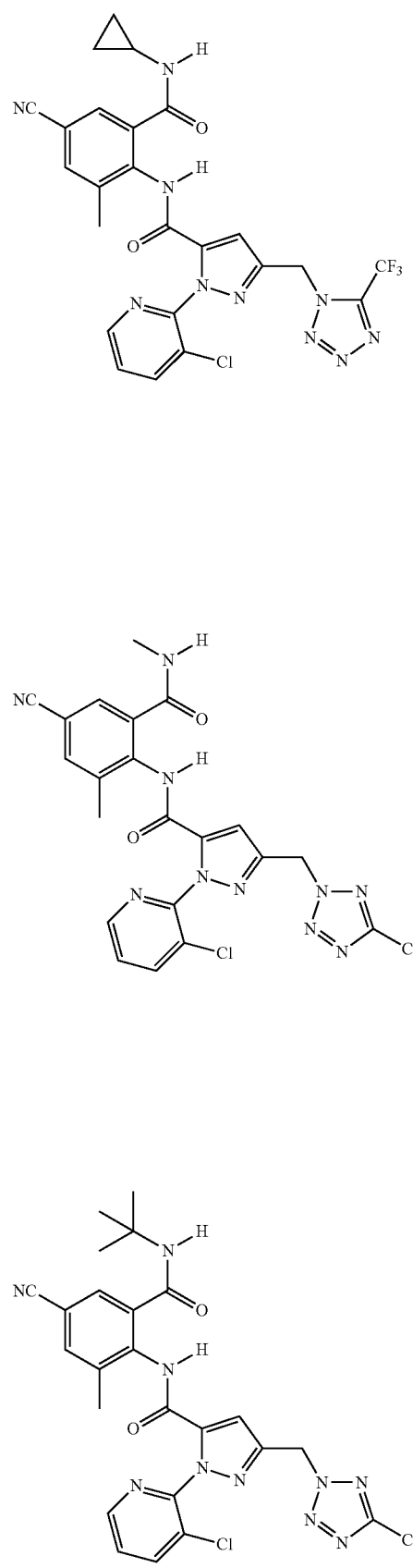
(I-1-12)
(I-1-13)
(I-1-14)

(I-1-15)
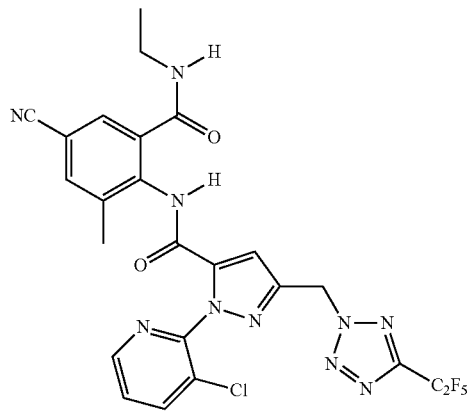
(I-1-16)
(I-1-17)
(I-1-18)
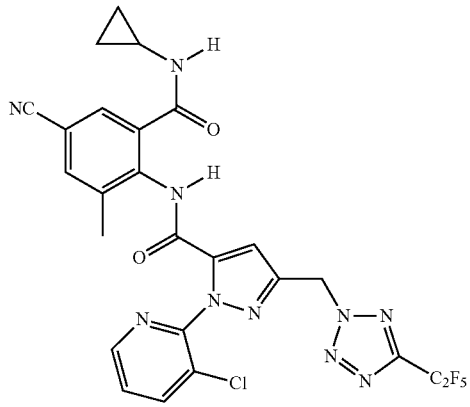
(I-1-19)
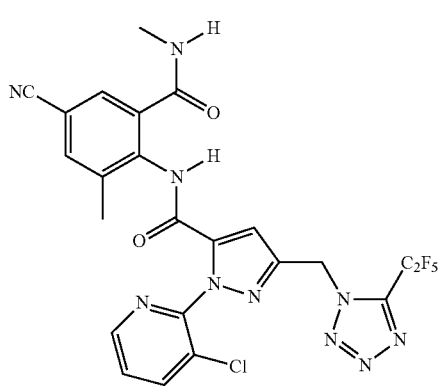
(I-1-20)
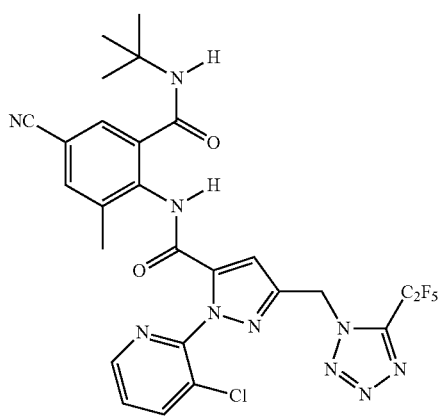
(I-1-21)
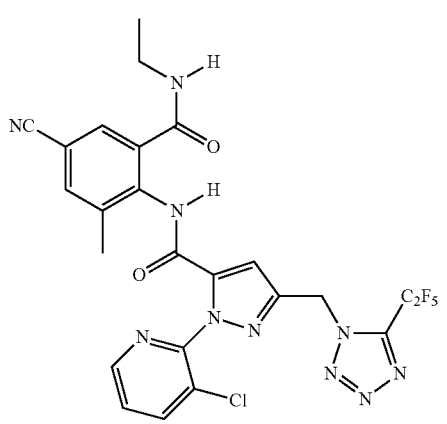

-continued
(I-1-22)
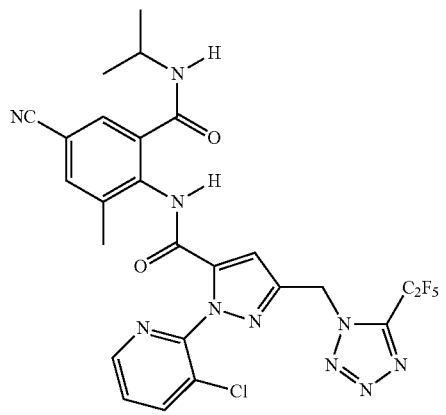
(I-1-23)
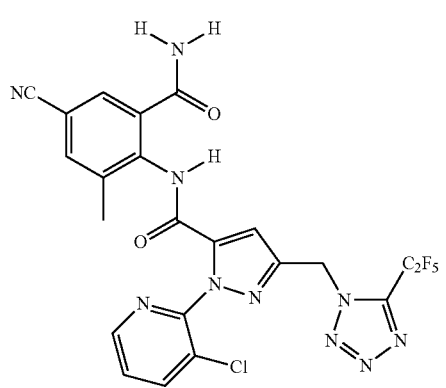
(I-1-24)
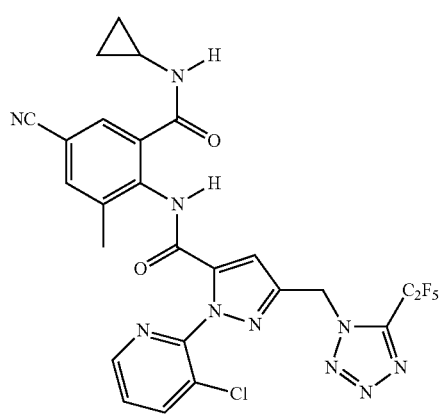
(I-1-25)
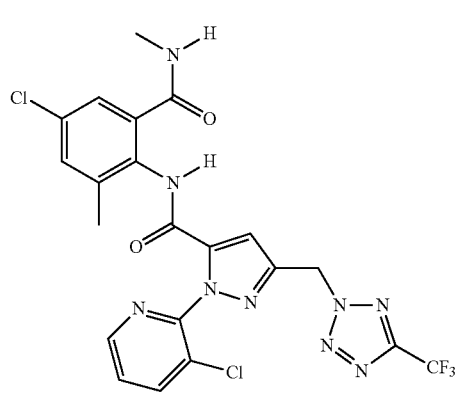
-continued
(I-1-26)
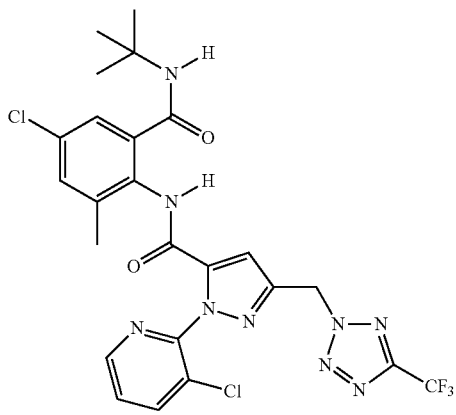
(I-1-27)
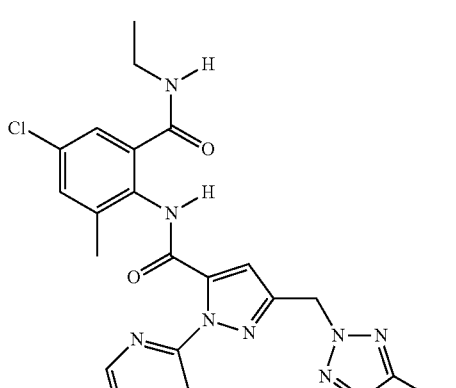
(I-1-28)
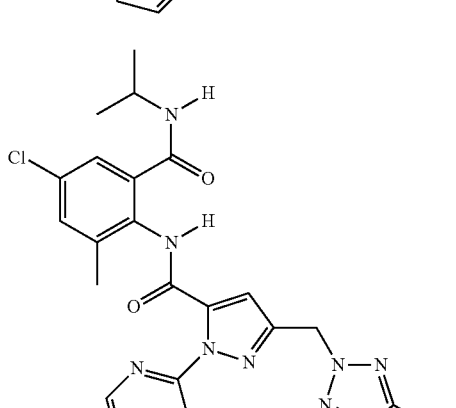
(I-1-29)
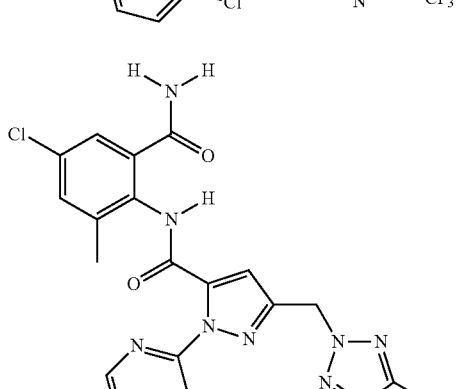

-continued
(I-1-30)
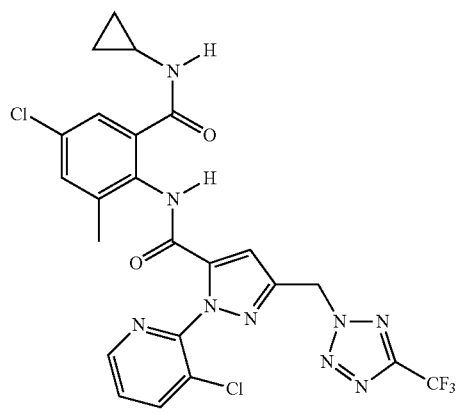
(I-1-31)
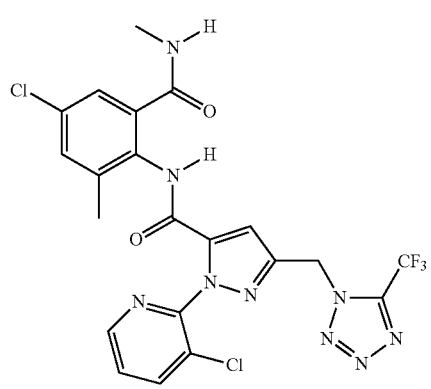
(I-1-32)
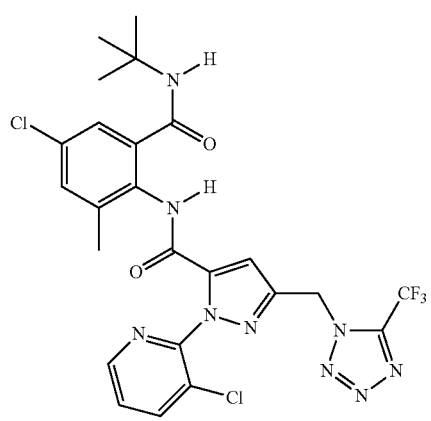
(I-1-33)
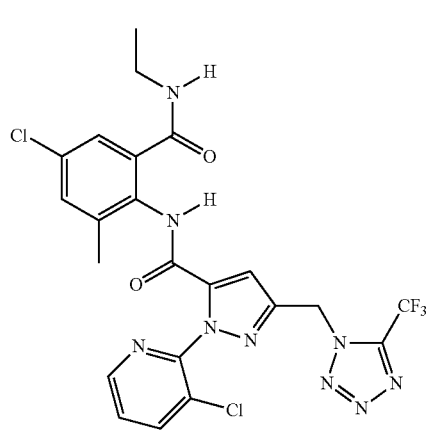
(I-1-34)
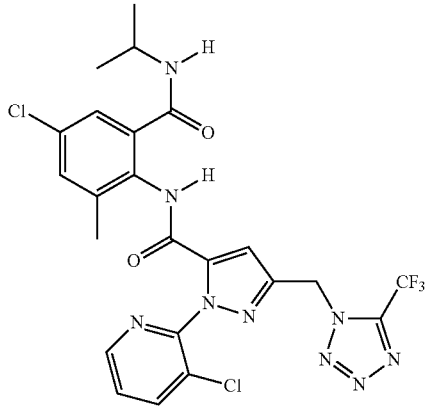
(I-1-35)
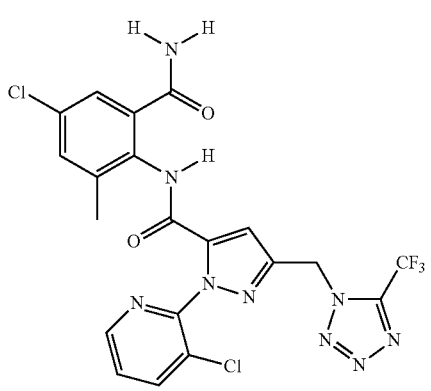
(I-1-36)
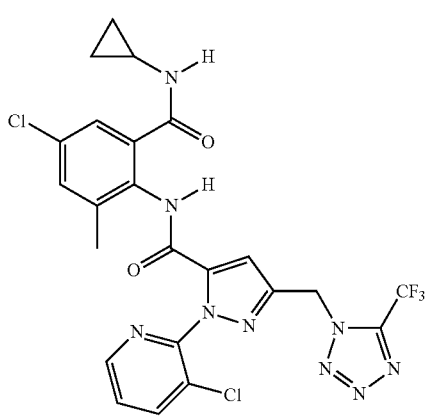
(I-1-37)
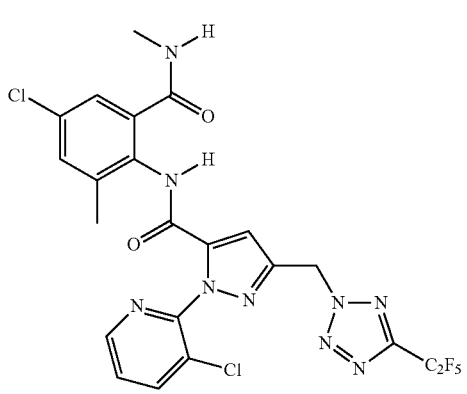

(I-1-38)
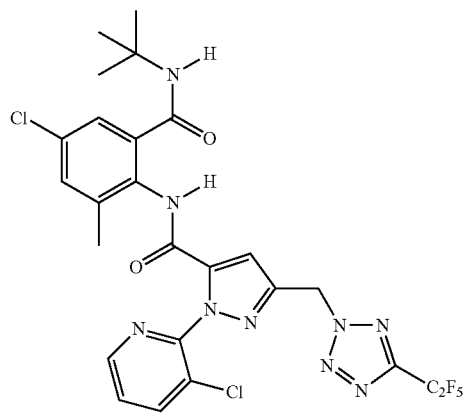
(I-1-39)
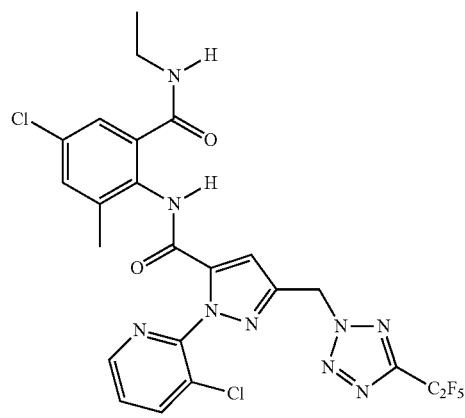
(I-1-40)
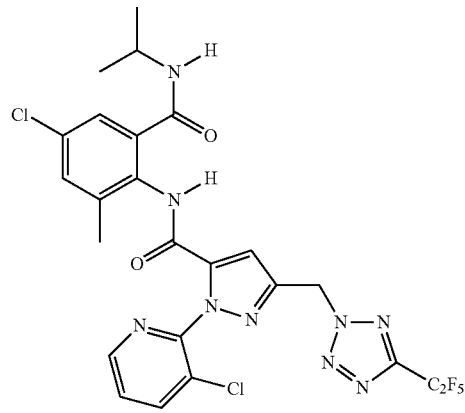
(I-1-41)
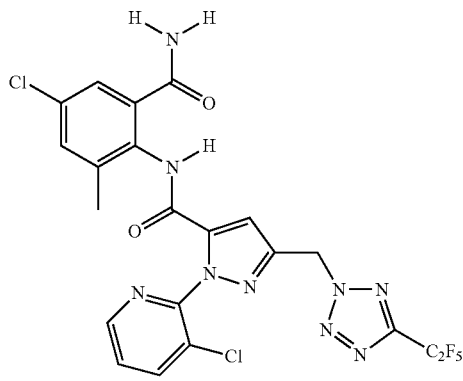
(I-1-42)
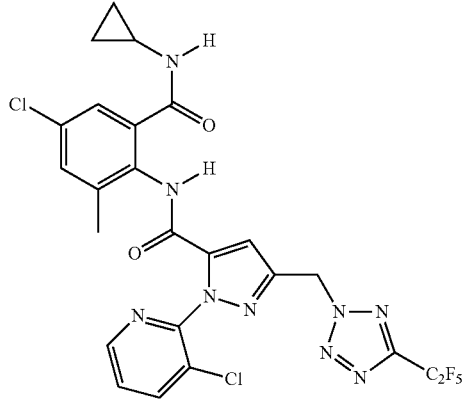
(I-1-43)
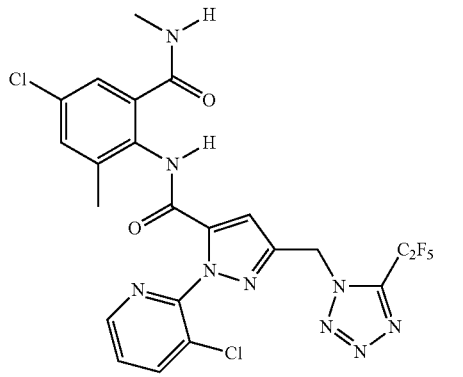
(I-1-44)
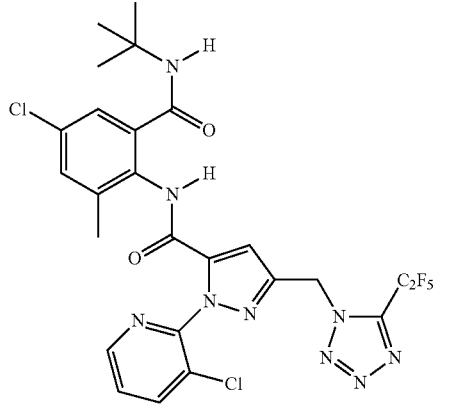

-continued
(I-1-45)
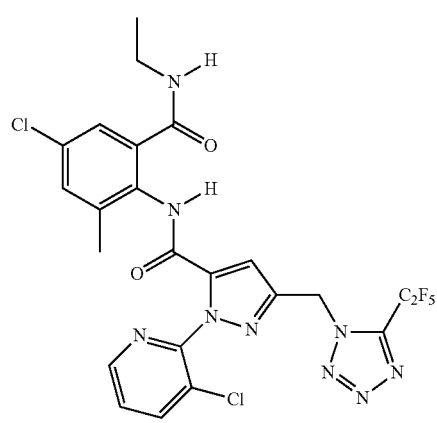
(I-1-46)
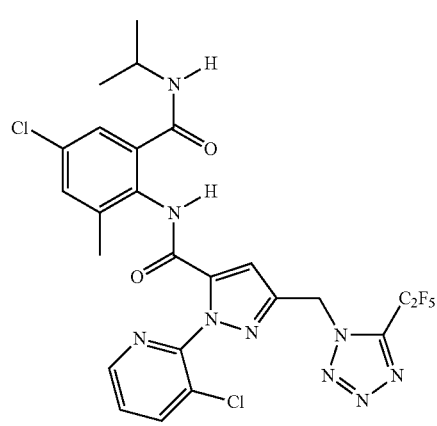
(I-1-47)
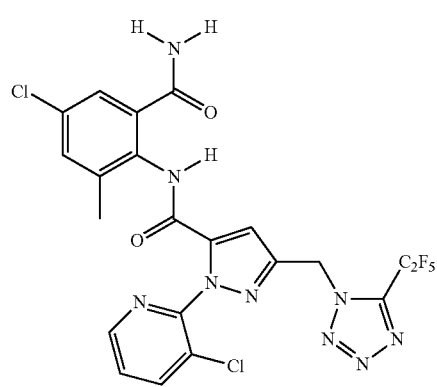
(I-1-48)
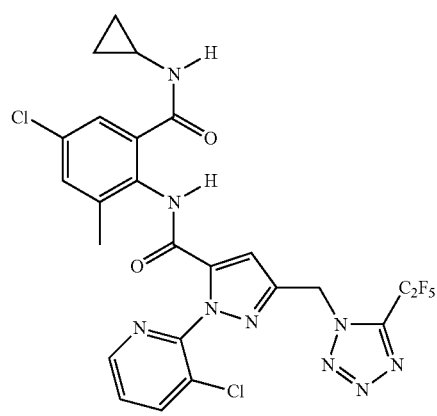
(I-1-49)
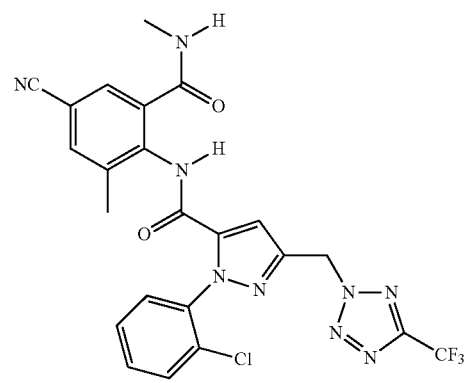
(I-1-50)
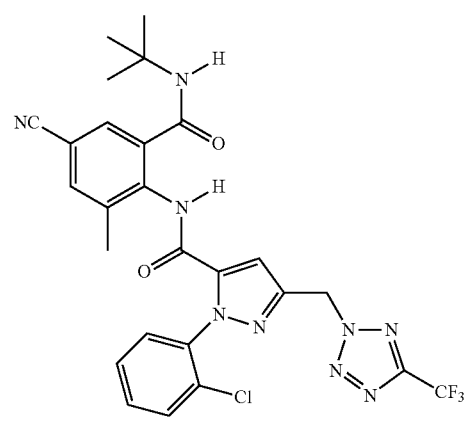
(I-1-51)
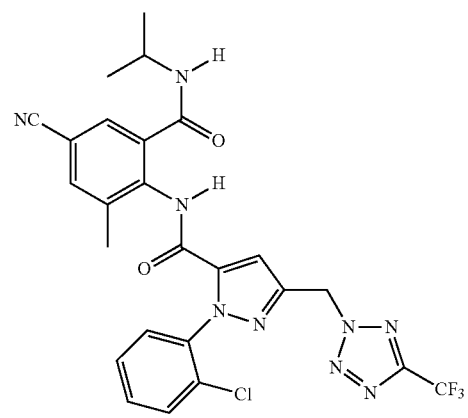
(I-1-52)
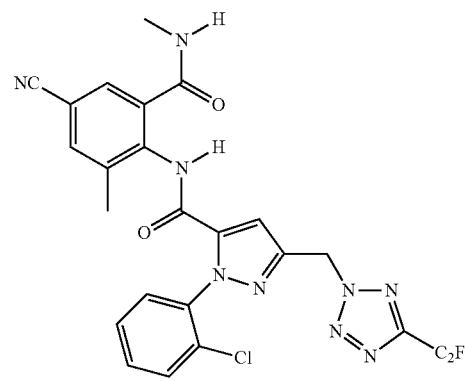

(I-1-53)
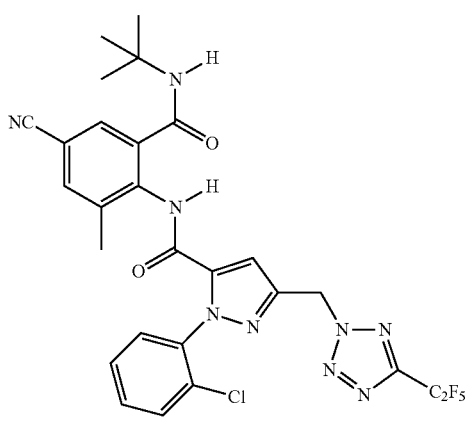
(I-1-54)
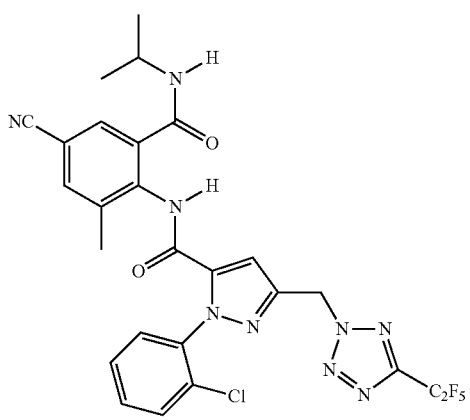
(I-1-55)
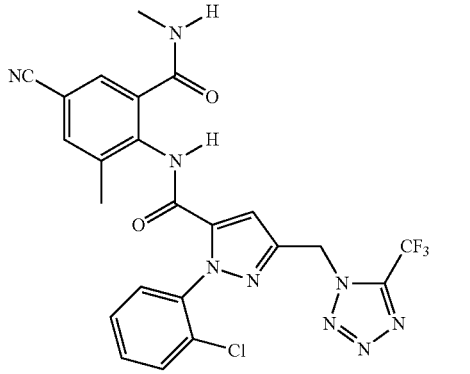
(I-1-56)
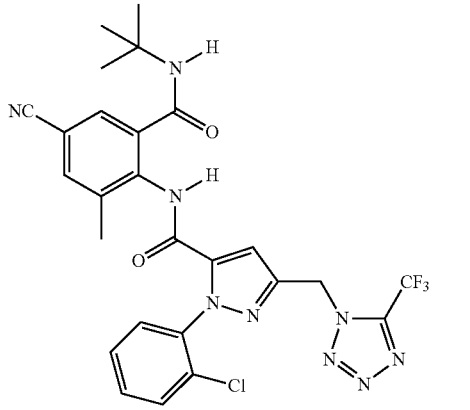
(I-1-57)
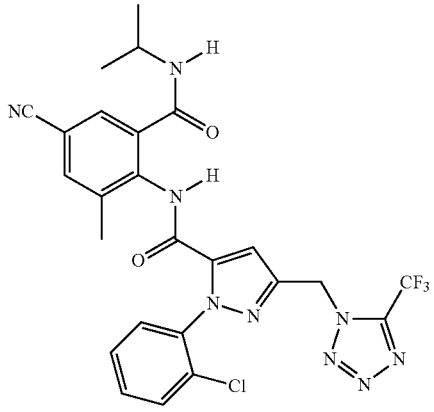
(I-1-58)
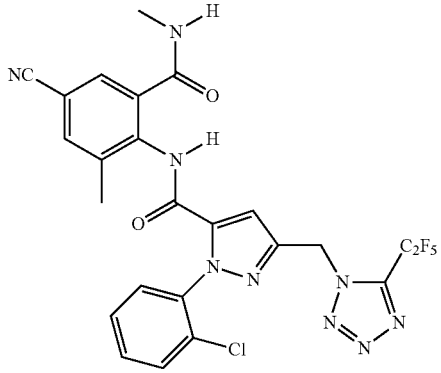
(I-1-59)
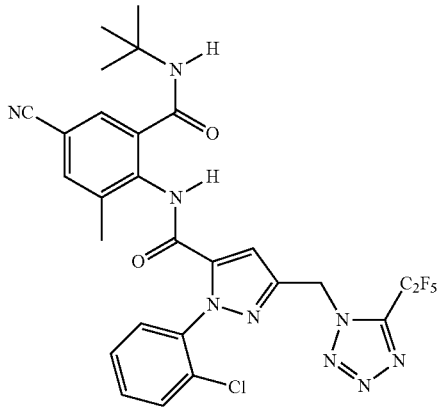
(I-1-60)
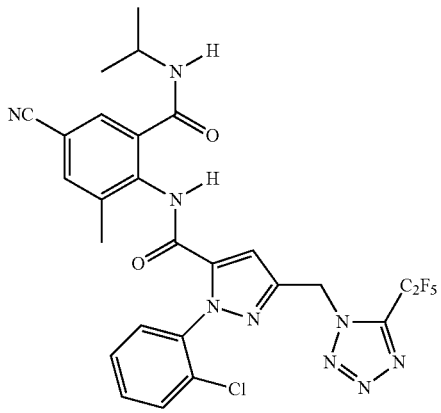

(I-1-61)
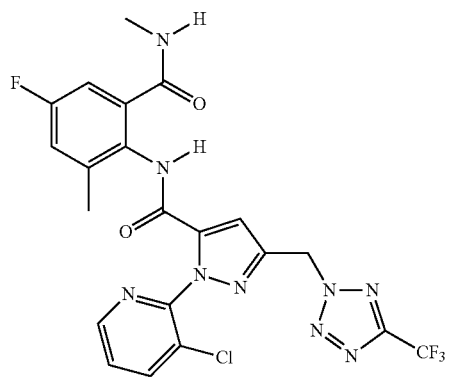
(I-1-62)
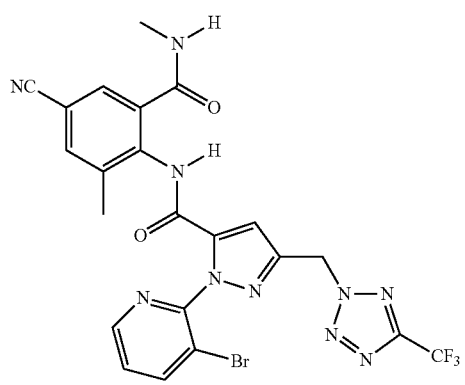
(I-1-63)
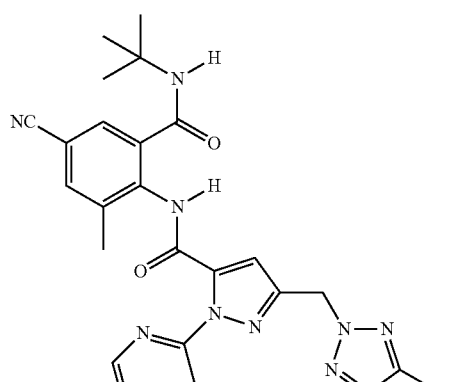
(I-1-64)
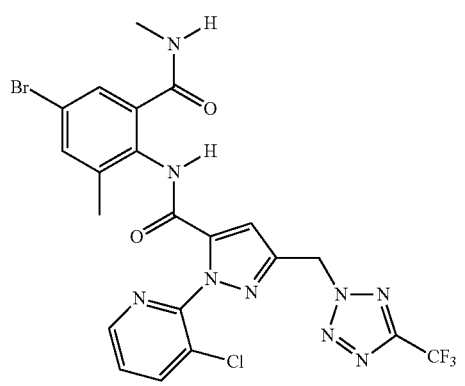
(I-1-65)
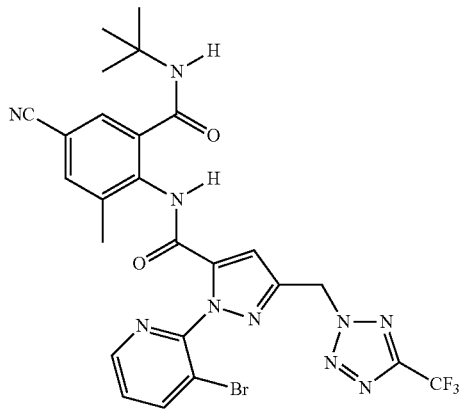
(I-1-66)
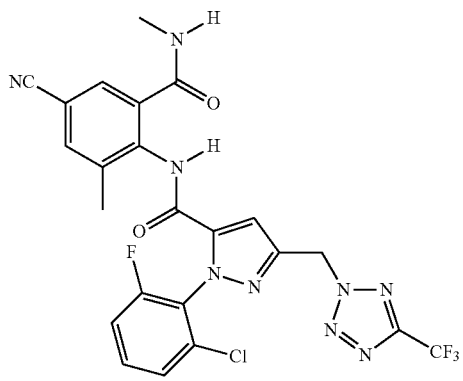
(I-1-67)
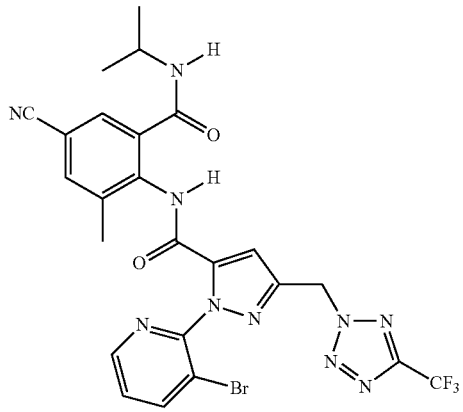
(I-1-68)
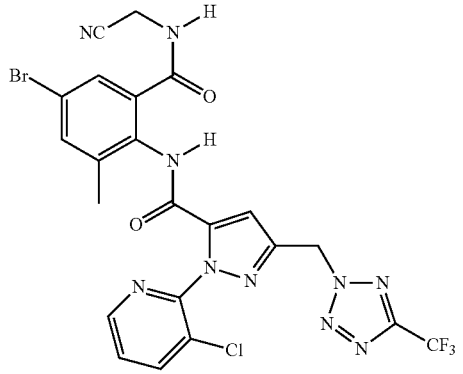

-continued

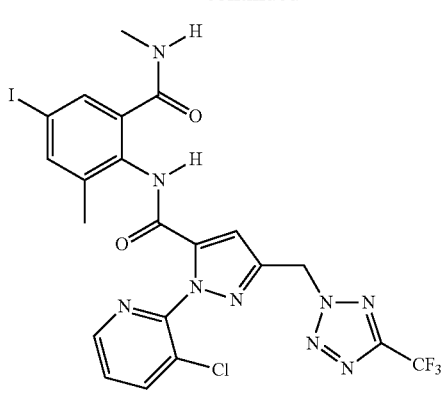
(I-1-69)

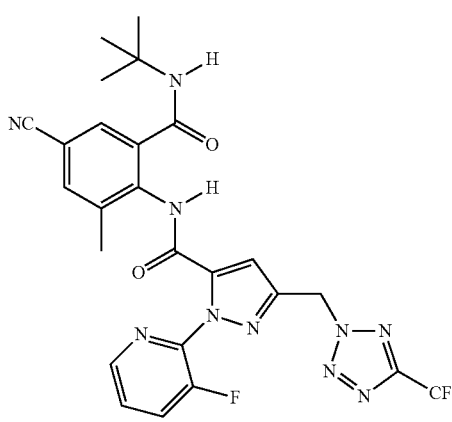
(I-1-70)

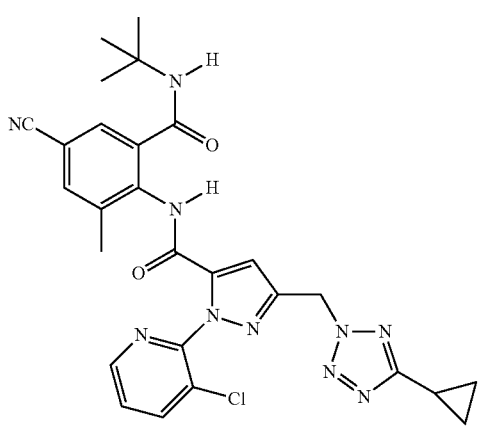
(I-1-71)

For the use according to the invention, particular preference is likewise given to mixtures of the active compounds of the formulae (I-1-1) to (I-1-71) below.

These mixtures are preferably present in a mixing ratio of from 80:20 to 99:1. In an exemplary manner, mention may be made of the mixture I-1-1/I-1-7, where the compound of the formula I-1-1 and the compound of the formula I-1-7 are present in a mixing ratio from 80:20 to 99:1. In an exemplary manner, mention may also be made of the mixture I-1-2/I-1-8, where the compound of the formula I-1-2 and the compound of the formula I-1-8 are present in a mixing ratio from 80:20 to 99:1.

I-1-1-/I-1-7,
I-1-2/I-1-8,
I-1-3/I-1-9,
I-1-4/I-1-10,
I-1-5/I-1-11,
I-1-6/I-1-12,
I-1-13/I-1-1-19,
I-1-14/I-1-20,
I-1-15/I-1-21,
I-1-17/I-1-23,
I-1-18/I-1-24,
I-1-25/I-1-31,
I-1-26/I-1-32,
I-1-27/I-1-33,
I-1-28/I-1-34,
I-1-29/I-1-35,
I-1-30/I-1-36,
I-1-37/I-1-43,
I-1-38/I-1-44,
I-1-39/I-1-45,
I-1-40/I-1-46,
I-1-41/I-1-47,
I-1-42/I-1-48,
I-1-49/I-1-55,
I-1-50/I-1-56,
I-1-51/I-1-57,
I-1-52/I-1-58,
I-1-53/I-1-59,
I-1-54/I-1-60.

For the use according to the invention very particular preference is given to the active compounds of the formula (I-1) or mixtures of active compounds of the formulae (I-1-1) to (I-1-71) listed below:

(I-1-1), (I-1-2), (I-1-3), (I-1-61), (I-1-62), (I-1-63), (I-1-64), (I-1-65), (I-1-66), (I-1-67), (I-1-68), (I-1-69), (I-1-70), (I-1-71), I-1-1/I-1-7, I-1-2/I-1-8, I-1-3/I-1-9. The use according to the invention of the anthranilamide derivatives is against a wide range of animal pests, in particular insects, archnids, helminths, nematodes and molluscs encountered in agriculture, in horticulture, in forests and in gardens and leisure facilities, against normally sensitive and resistant species and against all or individual development stages. These pests include:

pests from the phylum of the Arthropoda, in particular from the class of the Arachnida, for example *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia graminum*, *Bryobia praetiosa*, *Centruroides* spp., *Chorioptes* spp., *Dermanyssus gallinae*, *Dermatophagoides pteronyssinus*, *Dermatophagoides farinae*, *Dermacentor* spp., *Eotetranychus* spp., *Epitrimerus pyri*, *Eutetranychus* spp., *Eriophycs* spp., *Glycyphagus domesticus*, *Halotydeus destructor*, *Hemitarsonemus* spp., *Hyalomma* spp., *Ixodes* spp., *Latrodectus* spp., *Loxosceles* spp., *Metatetranychus* spp., *Neutrombicula autumnalis*, *Nuphersa* spp., *Oligonychus* spp., *Ornithodorus* spp., *Ornithonyssus* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Steneotarsonemus* spp., *Steneotarsonemus spinki*, *Tarsonemus* spp., *Tetranychus* spp., *Trombicula alfreddugesi*, *Vacjovis* spp., *Vasates lycopersici*.

From the class of the Chilopoda, for example, *Geophilus* spp., *Scutigera* spp.

From the order or the class of the Collembola, for example, *Onychiurus armatus*.

From the class of the Diplopoda, for example, *Blaniulus guttulatus*.

From the class of the insects, for example from the order of the Blattodca, for example *Blattella asahinai*, *Blattella ger-* manica, *Blatta orientalis, Leucophaea maderae, Panchlora* spp., *Parcoblatta* spp., *Periplaneta* spp., *Supella longipalpa*.

From the order of the Coleoptera, for example, *Acalymma vittatum, Acanthoscelides obtectus, Adoretus* spp., *Agelastica alni, Agriotes* spp., *Alphitobius diaperinus, Amphimallon solstitialis, Anobium punctatum, Anoplophora* spp., *Anthonomus* spp., *Anthrenus* spp., *Apion* spp., *Apogonia* spp., *Atomaria* spp., *Attagenus* spp., *Bruchidius obtectus, Bruchus* spp., *Cassida* spp., *Cerotoma trifurcata, Ceutorrhynchus* spp., *Chaetocncma* spp., *Cleonus mendicus, Conoderus* spp., *Cosmopolites* spp., *Costelytra zealandica, Ctenicera* spp., *Curculio* spp., *Cryptolestes ferruginous, Cryptorhynchus lapathi, Cylindrocopturus* spp., *Dermestes* spp., *Diabrotica* spp., *Dichocrocis* spp., *Dicladispa armigera, Diloboderus* spp., *Epilachna* spp., *Epitrix* spp., *Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., *Lachnostema consanguinca, Lasioderma sericome, Latheticus oryzac, Lathridius* spp., *Lema* spp., *Leptinotarsa decemlineata, Leucoptera* spp., *Lissorhoptrus oryzophilus, Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Necrobia* spp., *Niptus hololcucus, Oryctes rhinoceros, Oryzacphilus surinamensis, Oryzaphagus oryzac, Otiorrhynchus* spp., *Oxycctonia jucunda, Phaedon cochleariae, Phyllophaga* spp., *Phyllophaga helleri, Phyllotreta* spp., *Popillia japonica, Premnotrypes* spp., *Prostephanus truncates, Psylliodes* spp., *Ptinus* spp., *Rhizobius ventralis, Rhizopertha dominica, Sitophilus* spp., *Sitophilus oryzae, Sphenophorus* spp., *Stegobium paniceum, Stemechus* spp., *Symphyletes* spp., *Tanymecus* spp., *Tenebrio molitor, Tenebrioides mauretanicus, Tribolium* spp., *Trogoderma* spp., *Tychius* spp., *Xylotrechus* spp., *Zabrus* spp.

From the order of the Diptera, for example, *Aedes* spp., *Agromyza* spp., *Anastrepha* spp., *Anopheles* spp., *Asphondylia* spp., *Bactrocera* spp., *Bibio hortulanus, Calliphora erythrocephala, Calliphora vicina, Ceratitis capitata, Chironomus* spp., *Chrysomyia* spp., *Chrysops* spp., *Chrysozona pluvialis, Cochliomyia* spp., *Contarinia* spp., *Cordylobia anthropophaga, Cricotopus sylvestris, Culex* spp., *Culicoides* spp., *Culiseta* spp., *Cuterebra* spp., *Dacus oleae, Dasyneura* spp., *Delia* spp., *Dermatobia hominis, Drosophila* spp., *Echinocnemus* spp., *Fannia* spp., *Gasterophilus* spp., *Glossina* spp., *Haematopota* spp., *Hydrellia* spp., *Hydrellia griscola, Hylemya* spp., *Hippobosca* spp., *Hypoderma* spp., *Liriomyza* spp. *Lucilia* spp., *Lutzomyia* spp., *Mansonia* spp., *Musca* spp., *Oestrus* spp., *Oscinella frit, Paratanytarsus* spp., *Paralauterborniella subcincta, Pegomyia* spp., *Phlebotomus* spp., *Phorbia* spp., *Phormia* spp., *Piophila casci, Prodiplosis* spp., *Psila rosac, Rhagoletis* spp., *Sarcophaga* spp., *Simulium* spp. *Stomoxys* spp., *Tabanus* spp., *Tetanops* spp., *Tipula* spp.

From the order of the Heteroptera, for example, *Anasa tristis, Antestiopsis* spp., *Boisea* spp., *Blissus* spp., *Calocoris* spp., *Campylomma livida, Cavelerius* spp., *Cimex* spp., *Collaria* spp., *Creontiades dilutus, Dasynus piperis, Dichelcias furcatus, Diconocoris hewetti. Dysdercus* spp., *Euschistus* spp., *Eurygaster* spp., *Heliopeltis* spp., *Horcias nobilellus, Leptocorisa* spp., *Leptocorisa vancorms, Leptoglossus phyllopus, Lygus* spp., *Macropes excavatus, Miridac, Monalonion atratum, Nezara* spp., *Ocbalus* spp., *Pentomidae, Piesma quadrata, Piezodorus* spp., *Psallus* spp., *Pseudacysta persca, Rhodnius* spp., *Sahlbergella singularis, Scaptocoris castanea, Scotinophora* spp., *Stephanitis nashi, Tibraca* spp., *Triatoma* spp.

From the order of the Homoptera, for example, *Acizzia acaciaebaileyanae, Acizzia dodonaeae, Acizzia uncatoides, Acrida turrita, Acyrthosipon* spp., *Acrogonia* spp., *Aeneolamia* spp., *Agonoscena* spp., *Aleyrodes proletella, Aleurolobus barodensis, Aleurothrixus floccosus, Allocaridara malayensis, Amrasca* spp., *Anuraphis cardui, Aonidiella* spp., *Aphanostigma piri, Aphis* spp., *Arboridia apicalis, Arytainilla* spp., *Aspidiella* spp., *Aspidiotus* spp., *Atanus* spp., *Aulacorthum solani, Bemisia tabaci, Blastopsylla occidentalis, Borcioglycaspis melalcucae, Brachycaudus helichrysi, Brachycolus* spp., *Brevicoryne brassicae, Cacopsylla* spp., *Calligypona marginata, Cameocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus ficus, Cicadulina mbila, Coccomytilus halli, Coccus* spp., *Cryptomyzus ribis, Cryptoneossa* spp., *Ctenarytaina* spp., *Dalbulus* spp., *Dialcurodes citri, Diaphorina citri, Diaspis* spp., *Drosicha* spp., *Dysaphis* spp., *Dysmicoccus* spp., *Empoasca* spp., *Eriosoma* spp., *Erythroneura* spp., *Eucalyptolyma* spp., *Euphyllura* spp., *Euscelis bilobatus, Ferrisia* spp., *Geococcus coffeae, Glycaspis* spp., *Heteropsylla cubana, Heteropsylla spinulosa, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Macrosteles facifrons, Mahanarva* spp., *Melanaphis sacchari, Metcalfiella* spp., *Metopolophium dirhodum, Monellia costalis, Monclliopsis pecanis, Myzus* spp., *Nasonovia ribisnigri, Nephotettix* spp., *Nettigoniclla spectra, Nilaparvata lugens, Oncometopia* spp., *Onhezia praelonga, Oxya chinensis, Pachypsylla* spp., *Parabemisia myricas, Paratrioza* spp., *Parlatoria* spp., *Pemphigus* spp., *Percgrinus maidis, Phenacoccus* spp., *Phlocomyzus passerinii, Phorodon humuli, Phylloxera* spp., *Pinnaspis aspidistras, Planococcus* spp., *Prosopidopsylla flava, Protopulvinaria pyriformis, Pseudaulacaspis pentagona, Pseudococcus* spp., *Psyllopsis* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoideus titanus, Schizaphis graminum, Selenaspidus articulatus, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., *Trialcurodes vaporariorum, Trioza* spp., *Typhlocyba* spp., *Unaspis* spp., *Vitcus vitifolii, Zygina* spp.

From the order of the Hymenoptera, for example, *Acromyrmex* spp., *Athalia* spp., *Atta* spp., *Diprion* spp., *Hoplocampa* spp., *Lasius* spp., *Monomorium pharaonis, Sirex* spp., *Solenopsis invieta, Tapinoma* spp., *Urocerus* spp., *Vespa* spp., *Xeris* spp.

From the order of the Isopoda, for example, *Armadillidium vulgare, Oniscus asellus, Porcellio scaber.*

From the order of the Isoptera, for example, *Coptotermes* spp., *Cornitermes cumulans, Cryptotermes* spp., *Incisitermes* spp., *Microtermes obesi, Odontotermes* spp., *Reticulitermes* spp.

From the order of the Lepidoptera, for example, *Achroia grisella, Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busscola* spp., *Cacoecia* spp., *Caloptilia theivora, Capua reticulana, Carpocapsa pomonella, Carposina niponensis, Cheimatobia brumata, Chilo* spp., *Choristoneura* spp., *Clysia ambiguella, Cnaphalocerus* spp., *Cnaphalocrocis medinalis, Cnephasia* spp., *Conopomorpha* spp., *Conotrach-* elus spp., *Copitarsia* spp., *Cydia* spp., *Dalaca noctuides*, *Diaphania* spp., *Diatraca saccharalis*, *Earias* spp., *Ecdytolopha aurantium*, *Elasmopalpus lignoscllus*, *Eldana saccharina*, *Ephestia* spp., *Epinotia* spp., *Epiphyas postvittana*, *Etiella* spp., *Eulia* spp., *Eupoecilia ambiguella*, *Euproctis* spp., *Euxoa* spp., *Feltia* spp., *Galleria mellonella*, *Gracillaria* spp., *Grapholitha* spp., *Hedylepta* spp., *Helicoverpa* spp., *Heliothis* spp., *Hofmannophila pseudospretella*, *Homoeosoma* spp., *Homona* spp., *Hyponomeuta padella*, *Kakivoria flavolasciata*, *Laphygma* spp., *Laspeyresia molesta*, *Leucinodes orbonalis*, *Leucoptera* spp., *Lithocolletis*, spp., *Lithophane antennata*, *Lobesia* spp., *Loxagrotis albicosta*, *Lymantria* spp., *Lyonetia* spp., *Malacosoma neustria*, *Maruca testulalis*, *Mamstra brassicae*, *Melanitis leda*, *Mocis* spp., *Monopis obviella*, *Mythimna separata*, *Nemapogon cloacellus*, *Nymphula* spp., *Oiketicus* spp., *Oria* spp., *Orthaga* spp., *Ostrinia* spp., *Oulema oryzae*, *Panolis flammea*, *Parnara* spp., *Pectinophora* spp., *Perileucoptera* spp., *Phthorimaea* spp., *Phyllocnistis citrella*, *Phyllonorycter* spp., *Pieris* spp., *Platynota stultana*, *Plodia interpunctella*, *Plusia* spp., *Plutella xylostella*, *Prays* spp., *Prodenia* spp., *Protoparce* spp., *Pseudaletia* spp., *Pseudaletia unipuncta*, *Pseudoplusia includens*, *Pyrausta nubilalis*, *Rachiplusia nu*, *Schoenobius* spp., *Scirpophaga* spp., *Scirpophaga innotata*, *Scotia segetum*, *Sesamia* spp., *Sesamia inferens*, *Sparganothis* spp., *Spodoptera* spp., *Spodoptera pracfica*, *Stathmopoda* spp., *Stomopteryx subsecivella*, *Synanthedon* spp., *Tecia solanivora*, *Therrnesia gemmatalis*, *Tinea cloacella*, *Tinea pellionella*, *Tineola bisselliella*, *Tortrix* spp., *Trichophaga tapetzella*, *Trichoplusia* spp., *Tryporyza incertulas*, *Tuta absoluta*, *Virachola* spp.

From the order of the Orthoptera or Saltatoria, for example, *Acheta domesticus*, *Dichroplus* spp., *Gryllotalpa* spp., *Hieroglyphus* spp., *Locusta* spp., *Melanoplus* spp., *Schistocerca gregaria*.

From the order of the Phthiraptera, for example. *Damalinia* spp., *Haematopinus* spp., *Linognathus* spp., *Pediculus* spp., *Phylloera vastatrix*, *Pthirus pubis*, *Trichodectes* spp.

From the order of the Psocoptera, for example, *Lepinotus* spp., *Liposcelis* spp.

From the order of the Siphonaptera, for example, *Ceratophyllus* spp., *Ctenocephalides* spp., *Pulex irritans*, *Tunga penetrans*, *Xenopsylla cheopsis*.

From the order of the Thysanoptcra, for example, *Anaphothrips obscurus*, *Baliothrips biformis*, *Drepanothrips reuteri*, *Enncothrips flavens*, *Frankliniella* spp., *Heliothrips* spp., *Hercinothrips femoralis*, *Rhipiphorothrips cruentatus*, *Scirtothrips* spp., *Taeniothrips cardamoni*, *Thrips* spp.

From the order of the Zygentoma (=Thysanura), for example. *Ctenolepisma* spp., *Lepisma saccharina*, *Lepismodes inquilinus*, *Thermobia domestica*.

From the class of the Symphyla, for example, *Scutigerella* spp.

Pests from the phylum of the Mollusca, in particular from the class of the Bivalvia, for example *Dreissena* spp., and also from the class of the Gastropoda, for example *Arion* spp., *Biomphalaria* spp., *Bulinus* spp., *Deroceras* spp., *Galba* spp., *Lymnaea* spp., *Oncomelania* spp., *Pomacca* spp., *Succinea* spp.

Animal parasites from the phyla of the Plathelminthcs and Nematoda, for example *Ancylostoma duodenale*, *Ancylostoma ceylanicum*, *Acylostoma brazilicnsis*, *Ancylostoma* spp., *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium Tatum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp, *Strongyloides fuellebonti*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

Plant pests from the phylum of the Nematoda. i.e. phytoparasitic nematodes, in particular *Aphelcnchoides* spp., *Bursaphelenchus* spp., *Ditylenchus* spp., *Globodcra* spp., *Heterodera* spp., *Longidorus* spp., *Meloidogyne* spp., *Pratylenchus* spp., *Radopholus* spp., *Trichodorus* spp., *Tylenchulus* spp, *Xiphinema* spp., *Helicotylenchus* spp., *Tylenchorhynchus* spp., *Scutelloncma* spp., *Paratrichodorus* spp., *Meloinema* spp., *Paraphelenchus* spp., *Aglenchus* spp., *Belonolaimus* spp., *Nacobbus* spp, *Rotylenchulus* spp., *Rotylenchus* spp., *Neotylenchus* spp., *Paraphelenchus* spp., *Dolichodorus* spp., *Hoplolaimus* spp., *Punctodcra* spp., *Criconemella* spp., *Quinisulcius* spp., *Hemicycliophora* spp., *Anguina* spp., *Subanguina* spp., *Hemicriconemoides* spp., *Psilenchus* spp., *Pseudohalenchus* spp., *Criconemoides* spp., *Cacopaurus* spp.

It is furthermore possible to control, from the subkingdom of the Protozoa, the order of the Coccidia, for example *Eimeria* spp.

The present invention further provides an application solution for treatment of plants, comprising an amount, effective for enhancement of the resistance of plants to abiotic stress factors, of at least one compound selected from the group consisting of anthranilamide derivatives of the general formula (I). Abiotic stress conditions which can be relativized may include, for example, drought, cold and hot conditions, osmotic stress, waterlogging, elevated soil salinity, elevated exposure to minerals, ozone conditions, strong light conditions, limited availability of nitrogen nutrients, limited availability of phosphorus nutrients.

In one embodiment, for example, the anthranildamide derivatives provided in accordance with the invention may be applied by application to appropriate plants or parts of plants to be treated. The use of the compounds (I) according to the invention envisaged in accordance with the invention is effected preferably with a dosage between 0.0005 and 3 kg/ha, more preferably between 0.001 and 2 kg/ha, especially preferably between 0.005 and 1 kg/ha.

The term "resistance to abiotic stress" is understood in the context of the present invention to mean various kinds of advantages for plants. Such advantageous properties are manifested, for example, in the following improved plant characteristics: improved root growth with regard to surface area and depth, increased stolon and tiller formation, stronger and more productive stolons and tillers, improvement in shoot growth, increased lodging resistance, increased shoot base diameter, increased leaf area, higher yields of nutrients and constituents, for example carbohydrates, fats, oils, proteins, vitamins, minerals, essential oils, dyes, fibres, better fibre quality, earlier flowering, increased number of flowers, reduced content of toxic products such as mycotoxins, reduced content of residues or disadvantageous constituents of any kind, or better digestibility, improved storage stability of the harvested material, improved tolerance to disadvantageous temperatures, improved tolerance to drought and aridity, and also oxygen deficiency as a result of waterlogging, improved tolerance to elevated salt contents in soil and water, enhanced tolerance to ozone stress, improved compatibility with respect to herbicides and other crop treatment compositions, improved water absorption and photosynthesis performance, advantageous plant properties, for example acceleration of ripening, more homogeneous ripening, greater attractiveness to beneficial animals, improved pollination, or other advantages well known to a person skilled in the art.

More particularly, the use according to the invention exhibits the advantages described in application to plants and plant parts.

For the use according to the invention, it is furthermore possible to combine known substances having an effect on the maturation of the plant with the anthranilamide derivatives according to the invention. Here, mention may be made, for example, of the active compounds below (the compounds are referred to either by the "common name" in accordance with the International Organization for Standardization (ISO) or by the chemical name or by the code number), in each case including all use forms, such as acids, salts, esters and isomers, such as stereoisomers and optical isomers. Here, by way of example, one and in some cases a plurality of use forms are mentioned:

rhizobitoxine, 2-aminoethoxyvinyltheine (AVG), inethoxyvinylglycine (MVG), vinylglycine, aminooxyacetic acid, sinefungin, S-adenosylhomocysteine, 2-keto-4-methyl thiobutyrate, 2-(methoxy)-2-oxoethyl (isopropylidene)aminooxyacetate. 2-(hexyloxy)-2-oxoethyl (isopropylidene) aminooxyacetate, 2-(isopropyloxy)-2-oxoethyl (cyclohexylidene)aminooxyacetate, putrescine, spermidine, spermine, 1,8-diamino-4-aminoethyloctane, L-canaline, daminozide, methyl 1-aminocyclopropyl-1-carboxylate, N-methyl-1-aminocyclopropyl 1-carboxylic acid, 1-aminocyclopropyl-1-carboxamide, substituted 1-aminocyclopropyl-1-carboxylic acid derivatives as described in DE3335514, EP30287, DE2906507 or U.S. Pat. No. 5,123,951, 1-aminocyclopropyl-1-hydroxamic acid, 1-methylcyclopropene, 3-methylcyclopropene, 1-ethylcyclopropene, 1-n-propylcyclopropene, 1-cyclopropenylmethanol, carvone, eugenol Combination partners usable for the compounds according to the invention in mixture formulations or in tankmixes are, for example, known active compounds based on inhibition of, for example, 1-aminocyclopropane-1-carboxylate synthase, 1-aminocyclopropane-1-carboxylate oxidase and the ethylene receptors, for example ETR1, ETR2, ERS1, ERS2 or EIN4, as described, for example, in Biotechn. Adv. 2006, 24, 357-367; Bot. Bull. Acad. Sin. 199, 40, 1-7 or Plant Growth Reg. 1993, 13, 41-46 and literature cited therein.

For the use according to the invention, the anthranilamide derivatives may furthermore be combined with known substances which increase the tolerance of plants to abiotic stress, for example abscisic acid and analogues thereof (plant hormone) (Jones and Mansfield. 1970, J. Exp. Botany 21: 714-719; Bonham-Smith et al., 1988, Physiologia Plantanim 73: 27-30), fungicides, in particular from the group of the strobilurins or the succinate dehydrogenase inhibitors, the herbicide glyphosate, osmolytes such as, for example, glycine betaine or biochemical precursors thereof, for example choline derivatives (Chen et al., 2000, Plant Cell Environ 23: 609-618, Bergmann et al., DE-4103253), antioxidants such as, for example, naphthols and xanthines, azoles, for example methylazoles such as paclobutrazol (Morrison and Andrews, 1992, J Plant Growth Regul 11: 113-117; Imperial Chemical Industries PLC, 1985, Research Disclosure 259: 578-582), benzothiadiazole (CGA 2457(4; common name: acibenzolar-S-methyl; trade name: Bion®) (Achuo et al., Plant Pathology 53(1), 65-72, 2004; Tamblyn et al., Pesticide Science 55(6), 676-677, 1999; EP-OS 0313512), acetylsalicylic acid, sulphoximines, from the group of the oxylipins, for example, jasmonic acid (Walling, J. Plant Growth Regul. 19, 195-216, 2000), insecticides from the group of the nconicotinoids (chloronicotinyls), in particular imidacloprid (Brown et al., Beltwide Cotton Conference Proceedings 2231-2237, 2004).

As is known, the various advantages for plants, which have been mentioned further above, can be combined in parts, and generally applicable terms can be used to describe them. Such terms are, for example, the following names: phytotonic effect, resistance to stress factors, less plant stress, plant health, healthy plants, plant fitness, plant wellness, plant concept, vigour effect, stress shield, protective shield, crop health, crop health properties, crop health products, crop health management, crop health therapy, plant health, plant health properties, plant health products, plant health management, plant health therapy, greening effect or regreening effect, freshness, or other terms with which a person skilled in the art is quite familiar.

In the context of the present invention, a good effect on the resistance to abiotic stress is understood as meaning, but not by limitation, at least an emergence improved by generally 3%, especially more than 5%, particularly preferably more than 10%, at least a yield enhanced by generally 3%, especially more than 5%, particularly preferably more than 10%, at least a root development improved by generally 3%, especially more than 5%, particularly preferably more than 10%, at least a shoot size rising by generally 3%, especially more than 5%, particularly preferably more than 10%.

at least a leaf area increased by generally 3%, especially more than 5%, particularly preferably more than 10%, at least an emergence improved by generally 3%, especially more than 5%, particularly preferably more than 10%, at least a photosynthesis performance improved by generally 3%, especially more than 5%, particularly preferably more than 10%, and/or at least a flower formation improved by generally 3%, especially more than 5%, particularly preferably more than 10%, it being possible for the effects to manifest themselves individually or else in any combination of two or more effects.

The present invention further provides an application solution for treatment of plants, comprising an amount, effective for enhancement of the resistance of plants to abiotic stress factors, of at least one compound of the general formula (I). The application solution may comprise other customary constituents, such as solvents, formulation aids, especially water. Further constituents may include agrochemically active compounds described below.

The present invention further provides for the use of corresponding application solutions for increasing the resistance of plants to abiotic stress factors. The remarks which follow apply both to the use according to the invention of the compounds of the general formula (I) per se and to the corresponding application solutions.

All plants and plant parts can be treated in accordance with the invention. Plants are understood here to mean all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and vegetative and generative propagation material, for example cuttings, tubers, rhizomes, slips and seeds.

As already mentioned above, it is possible to treat all plants and their parts in accordance with the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

More preferably, plants of the plant cultivars which are each commercially available or in use are treated in accordance with the invention. Plant cultivars are to be understood as meaning plants having new properties ("traits") and which have been obtained by conventional breeding, by mutagenesis or by recombinant DNA techniques. They may be cultivars, biotypes and genotypes.

Depending on the plant species or plant cultivars, and the location and growth conditions (soils, climate, vegetation period, diet) thereof, the treatment according to the invention may also result in superadditive ("synergistic") effects. For example, possibilities include reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, increased flowering performance, easier harvesting, accelerated ripening, higher yields, higher quality and/or higher nutrient value of the harvested products, increased storage life and/or processibility of the harvested products, which exceed the effects actually to be expected.

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processibility of the harvested products. Further and particularly emphasized examples of such properties are an improved defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are increased defence of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the improved defence of plants against fungi, bacteria and viruses by systemic acquired resistance (SAR), systemin, phytoalexins, elicitors and also resistance genes and correspondingly expressed proteins and toxins. Traits that are additionally particularly emphasized are the increased tolerance of the plants to certain active herbicidal compounds, for example imidazolinones, sulphonylureas, glyphosate or phosphinothricin (for example the "PAT" gene). The genes which impart the desired traits in question may also be present in combinations with one another in the transgenic plants. Examples of "Bt plants" include maize varieties, cotton varieties, soya varieties and potato varieties which are sold under the trade names YIELD GARD® (for example maize, cotton, soya). KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance against glyphosate, for example maize, cotton, soya beans), Liberty Link® (tolerance against phosphinothricin, for example oilseed rape), IMI® (tolerance against imidazolinones) and STS® (tolerance against sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars which have these genetic traits or genetic traits which are still to be developed and will be developed and/or marketed in the future.

Plants and plant varieties which may also be treated according to the invention are those plants which are resistant to one or more abiotic stress factors. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

Plants and plant varieties which may also be treated according to the invention are those plants characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may likewise be treated according to the invention are hybrid plants that already express the characteristics of heterosis, or hybrid effect, which results in generally higher yield, vigour, health and resistance towards biotic and abiotic stress factors. Such plants are typically made by crossing an inbred male-sterile parent line (the female parent) with another inbred male-fertile parent line (the male parent). Hybrid seed is typically harvested from the male-sterile plants and sold to growers. Male-sterile plants can sometimes (e.g. in maize) be produced by detasseling (i.e. the mechanical removal of the male reproductive organs or male flowers) but, more typically, male sterility is the result of genetic determinants, in the plant genome. In that case, and especially when seed is the desired product to be harvested from the hybrid plants, it is typically useful to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described in *Brassica* species (WO 1992/005251, WO 1995/009910, WO 1998/27806, WO 2005/002324, WO 2006/021972 and U.S. Pat. No. 6,229,072). However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a bamase is selectively expressed in the tapetum cells in the stamens. Fertility can then be restored by expression in the tapetum cells of a ribonuclease inhibitor such as barstar (e.g. WO 1991/002069).

The anthranilamide derivatives can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

Accordingly, the present invention further relates to formulations and use forms prepared therefrom as crop protection compositions and/or pesticides, for example drench, drip and spray liquors, comprising at least one of the active compounds according the invention. In some cases, the use forms comprise further crop protection compositions and/or pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropyl guar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides. FAO Plant Production and Protection Papers—173, prepared by the FAO/WHO Joint Meeting on Pesticide Specifications, 2004, ISBN: 9251048576. The formulations optionally comprise, in addition to one or more active compounds according to the invention, further agrochemically active compounds.

These are preferably formulations or use forms which comprise auxiliaries, for example extenders, solvents, spontaneity promoters, carriers, emulsifiers, dispersants, frost protectants, biocides, thickeners and/or further auxiliaries, for example adjuvants. An adjuvant in this context is a component which enhances the biological effect of the formulation, without the component itself having a biological effect. Examples of adjuvants are agents which promote retention, spreading, attachment to the leaf surface or penetration.

These formulations are prepared in a known manner, for example by mixing the active compounds with auxiliaries such as, for example, extenders, solvents and/or solid carriers and/or further auxiliaries such as, for example, surfactants. The formulations are produced either in suitable plants or else before or during application.

Auxiliaries used may be substances capable of giving the formulation of the active compound, or the application forms prepared from these formulations (such as ready-to-use crop protection compositions, for example, such as drench, drip, spray liquors or seed dressings) particular properties, such as certain physical, technical and/or biological properties.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle it is possible to use all suitable solvents. Examples of suitable solvents are aromatic hydrocarbons, such as xylene, toluene or alkylnaphthalenes, chlorinated aromatic or chlorinated aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle it is possible to use all suitable carriers. Useful carriers include especially: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. Mixtures of such carriers may also be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, maize cobs and tobacco stalks.

Liquefied gaseous extenders or solvents can also be used. Particularly suitable extenders or carriers are those which are gaseous at ambient temperature and under atmospheric pressure, for example aerosol propellant gases, such as halohydrocarbons, and also butane, propane, nitrogen and carbon dioxide.

Examples of emulsifiers and/or foam formers, dispersants or wetting agents with ionic or nonionic properties, or mixtures of these surfactants, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkyl sulphonates, alkylsulphates, arylsulphonates, protein hydrolysates, lignosulphite waste liquors and methylcellulose. The presence of a surfactant is advantageous if one of the active compounds and/or one of the inert carriers is insoluble in water and when the application takes place in water.

It is possible to use colorants such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc as additional auxiliaries in the formulations and the use forms derived therefrom.

Stabilizers, such as low-temperature stabilizers, preservatives, antioxidants, light stabilizers or other agents which improve chemical and/or physical stability, may also be present. Foam formers or antifoams may also be present.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids may also be present as additional auxiliaries in the formulations and the use forms derived therefrom. Other possible auxiliaries are mineral and vegetable oils.

If appropriate, the formulations and the use forms derived therefrom may also comprise further auxiliaries. Examples of such additives include fragrances, protective colloids, binders, adhesives, thickeners, thixotropic agents, penetrants, retention promoters, stabilizers, sequestrants, complexing agents, humectants; spreaders. In general, the active compounds can be combined with any solid or liquid additive customarily used for formulation purposes.

Useful retention promoters include all those substances which reduce the dynamic surface tension, for example dioctyl sulphosuccinate, or increase the viscoelasticity, for example hydroxypropylguar polymers.

Useful penetrants in the present context are all those substances which are typically used to improve the penetration of agrochemically active compounds into plants. Penetrants are defined in this context by their ability to penetrate from the (generally aqueous) application liquor and/or from the spray coating into the cuticle of the plant and thereby increase the mobility of active compounds in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The active compound content of the use forms prepared from the commercially available formulations may vary within wide limits. The active compound concentration of the use forms may be from 0.0000001 to 95% by weight of active compound, preferably from 0.0001 to 1% by weight. The use according to the invention of the anthranilamides is by drenching, soil mixing, furrow treatment, in hydroponic or irrigation systems by drip application to the soil or other substrates, by soil, stem or flower injection, by planting hole treatment or by dip application, for example to propagation materials such as bulbs, tubers or roots, floating or seedbox application and, in particular in the case of seed, by single- or multilayer coating.

Preference according to the invention is given to the treatment of seed. Thus, most of the damage to crop plants which is caused by pests occurs as early as when the seed is infested during storage and after the seed is introduced into the soil, and during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of pests by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection products after sowing or after emergence of the plants. It is furthermore desirable to optimize the amount of active compound employed in such a way as to provide optimum protection for the seed and the germinating plant from attack by pests, but without damaging the plant itself by the active compound employed. In particular, methods for the treatment of seed should also take into consideration the intrinsic insecticidal properties of transgenic plants in order to achieve optimum protection of the seed and the germinating plant with a minimum of crop protection products being employed.

The present invention therefore in particular also relates to a method for the protection of seed and germinating plants, from attack by pests, by treating the seed with an active compound according to the invention. The invention likewise relates to the use of anthranilamides for the treatment of seed for protecting the seed and the plants resulting therefrom from pests. Furthermore, the invention relates to seed which has been treated according to the invention so as to afford protection from pests.

One of the advantages of the present invention is that the particular systemic properties of anthranilamide derivatives mean that treatment of the seed with these active compounds not only protects the seed itself, but also the resulting plants after emergence, from pests. In this manner, the immediate treatment of the crop at the time of sowing or shortly thereafter can be dispensed with.

Likewise, it must be considered as advantageous that according to the invention the anthranilamides can also be employed in particular in transgenic seed, the plants arising from this seed being capable of expressing a protein directed against pests. By treating such seed, certain pests can be controlled merely by the expression of the, for example, insecticidal protein, and additionally damage to the seed may be averted by the active compounds according to the invention.

The use according to the invention of the anthranilamide derivatives is suitable for protecting seed of any plant variety as already mentioned above which is employed in agriculture, in the greenhouse, in forests or in horticulture. In particular, this takes the form of seed of maize, peanut, canola, oilseed rape, poppy, soya beans, cotton, beet (for example sugar beet and fodder beet), rice, millet, wheat, barley, oats, rye, sunflower, tobacco, potatoes or vegetables (for example tomatoes, cabbage species). The active compounds according to the invention are likewise suitable for treating the seed of fruit plants and vegetables as already mentioned above. The treatment of the seed of maize, soya beans, cotton, wheat, rice and canola or oilseed rape is of particular importance.

As already mentioned above, the treatment of transgenic seed with active compounds according to the invention is also of particular importance. This takes the form of seed of plants which, as a rule, comprise at least one heterologous gene which governs the expression of a polypeptide with in particular insecticidal properties. In this context, the heterologous genes in transgenic seed may be derived from microorganisms such as *Bacillus, Rhizohium, Pseudomonas, Serratia, Trichoderma, Clavihacter, Glomus* or *Gliocladium*. The present invention is particularly suitable for the treatment of transgenic seed which comprises at least one heterologous gene originating from *Bacillus* sp. and whose gene product shows activity against the European corn borer and/or the corn root worm. It is particularly preferably a heterologous gene derived from *Bacillus thuringiensis*.

USE EXAMPLES

The examples below illustrate the invention, without limiting it in any way.

Example No. A

*Plutella xylostella* test on Savoy Cabbage; Drench Application
Solvent: 4 parts by weight of acetone
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. Savoy cabbage (*Brassica oleracea*) is watered with a solution of the product in question (volume of water: 60 ml/plant). The stated concentration refers to the amount of active compound per plant. After about 1 week, the treated plants are infested with larvae of the diamondback moth (*Plutella xylostella*). After 1 week, the activity in % is determined. 100% means that all caterpillars have been killed; 0% means that none of the caterpillars have been killed.

In this test, the following product showed good systemic action:

TABLE A

*Plutella x.* on Savoy cabbage

| Active compound | Concentration (mg of ai/plant) | Time at which the mortality is determined/days after infestation | % Activity (according to Abbott) |
| --- | --- | --- | --- |
| (I-1-3) according to the invention | 0.5 | 7 | 100 |
| (I-1-61) according to the invention | 0.5 | 7 | 100 |
| (I-1-62) according to the invention | 0.5 | 7 | 100 |
| (I-1-63) according to the invention | 0.5 | 7 | 100 |
| (I-1-64) according to the invention | 0.5 | 7 | 100 |
| (I-1-65) according to the invention | 1 | 7 | 100 |
| (I-1-66) according to the invention | 1 | 7 | 90 |
| (I-1-67) according to the invention | 1 | 7 | 100 |
| (I-1-68) according to the invention | 0.5 | 7 | 100 |
| (I-1-69) according to the invention | 0.5 | 7 | 100 |
| (I-1-70) according to the invention | 1 | 7 | 100 |
| (I-1-71) according to the invention | 0.5 | 7 | 90 |
| (I-1-1)/(I-1-7)* according to the invention | 2 | 7 | 100 |

*The mixture tested of compound (I-1-1)/compound (I-1-7) comprised about 85% of compound (I-1-1) and about 15% of compound (I-1-7).

Example No. B

*Spodoptera frugiperda* Test on Maize; Drench Application
Solvent: 4 parts by weight of acetone
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. Maize plants (*Zea mays*) are watered with a solution of the product in question (volume of water: 50 ml/plant). The stated concentration refers to the amount of active compound per plant. After about 1 week, the treated plants are infested with the armyworm (*Spodoptera frugiperda*). After 1 week, the activity in % is determined. 100% means that all caterpillars have been killed; 0% means that none of the caterpillars have been killed.

In this test, the following product showed good systemic action:

TABLE B

Spodoptera frugiperda on maize

| Active compound | Concentration (mg of ai/plant) | Time at which the mortality is determined/days after infestation | % Activity (according to Abbott) |
|---|---|---|---|
| (I-1-3) according to the invention | 0.5 | 7 | 100 |
| (I-1-61) according to the invention | 0.5 | 7 | 100 |
| (I-1-62) according to the invention | 0.5 | 7 | 98 |
| (I-1-63) according to the invention | 0.5 | 7 | 100 |
| (I-1-64) according to the invention | 0.5 | 7 | 100 |
| (I-1-65) according to the invention | 1 | 7 | 95 |
| (I-1-66) according to the invention | 1 | 7 | 95 |
| (I-1-67) according to the invention | 1 | 7 | 90 |
| (I-1-68) according to the invention | 0.5 | 7 | 100 |
| (I-1-69) according to the invention | 0.5 | 7 | 85 |
| (I-1-70) according to the invention | 1 | 7 | 90 |
| (I-1-71) according to the invention | 0.5 | 7 | 85 |
| (I-1-1):(I-1-7) * 85:15 according to the invention | 2 | 7 | 100 |

* The mixture tested of compound (I-1-1)/compound (I-1-7) comprised about 85% of compound (I-1-1) and about 15% of compound (I-1-7).

Example No. B-1

*Spodoptera fugiperda* Test on Maize; Drench Application

Solvent: 7 parts by weight of dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

Maize plants (*Zea mays*) are watered with a solution of the product in question and infested with the armyworm (*Spadoptera frugiperda*). After 14 days, the activity in % is determined. 100% means that all caterpillars have been killed; 0% means that none of the caterpillars have been killed.

In this test, the following product showed good systemic action:

TABLE B - 1

Spodoptera frugiperda on maize

| Active compound | Concentration (ppm) | Time at which the mortality is determined/days after treatment | % Activity (according to Abbott) |
|---|---|---|---|
| (I-1-2)/(I-1-8)* according to the invention | 4 | 14 | 100 |
| (I-1-1) according to the invention | 20 | 14 | 100 |
| (I-1-2) according to the invention | 20 | 14 | 100 |

*The mixture tested of compound (I-1-2)/compound (I-1-8) comprised about 84% of compound (I-1-2) and about 15% of compound (I-1-8).

Example No. C

*Heliothis armigera* Test on Cotton; Drench Application

Solvent: 4 parts by weight of acetone

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration. Cotton plants (*Gossypium hirsuium*) are watered with a solution of the product in question (volume of water: 50 ml/plant). The stated concentration refers to the amount of active compound per plant. After about 1 week, the treated plants are infested with larvae of the cotton bollworm (*Heliothis armigera*). After 1 week, the activity in % is determined. 100% means that all caterpillars have been killed; 0% means that none of the caterpillars have been killed.

In this test, the following product showed good systemic action:

TABLE C

Heliothis armigera on cotton

| Active compound | Concentration (mg of ai/plant) | Time at which the mortality is determined/days after infestation | % Activity (according to Abbott) |
|---|---|---|---|
| (I-1-3) according to the invention | 0.5 | 7 | 100 |
| (I-1-61) according to the invention | 0.5 | 7 | 100 |
| (I-1-62) according to the invention | 0.5 | 7 | 95 |
| (I-1-63) according to the invention | 0.5 | 7 | 100 |
| (I-1-64) according to the invention | 0.5 | 7 | 100 |
| (I-1-65) according to the invention | 1 | 7 | 100 |
| (I-1-66) according to the invention | 1 | 7 | 100 |

TABLE C-continued

Heliothis armigera on cotton

| Active compound | Concentration (mg of ai/plant) | Time at which the mortality is determined/days after infestation | % Activity (according to Abbott) |
|---|---|---|---|
| (I-1-67) according to the invention | 1 | 7 | 100 |
| (I-1-68) according to the invention | 0.5 | 7 | 100 |
| (I-1-69) according to the invention | 0.5 | 7 | 100 |
| (I-1-70) according to the invention | 1 | 7 | 95 |
| (I-1-1)/(I-1-7)* according to the invention | 2 | 7 | 100 |

*The mixture tested of compound (I-1-1)/compound (I-1-7) comprised about 85% of compound (I-1-1) and about 15% of compound (I-1-7).

Example No. D

*Myzus persicae* Test on Savoy Cabbage; Drench Application

Solvent: 7 parts by weight of dimethylformamide

Emulsifier: part by weight of alkylaryl polyglycol ether

To produce a suitable preparation of active compound, 1 part by weight of active compound is mixed with the stated amounts of solvent and emulsifier, and the concentrate is diluted with water to the desired concentration. Savoy cabbage (*Brassica oleracea*) heavily infested by the green peach aphid (*Myzus persicae*) is watered with a solution of the product of the desired concentration. After 10 days, the activity in % is determined. 100% means that all of the aphids have been killed: 0% means that none of the aphids have been killed.

In this test, the following product showed good systemic action:

TABLE D

Myzus persicae on Savoy cabbage

| Active compound | Concentration (ppm) | Time at which the mortality is determined/days after treatment | % Activity (according to Abbott) |
|---|---|---|---|
| (I-1-3) according to the invention | 20 | 10 | 90 |
| (I-1-62) according to the invention | 20 | 10 | 80 |
| (I-1-66) according to the invention | 20 | 10 | 90 |
| (I-1-1)/(I-1-7) * according to the invention | 20 | 10 | 100 |
| (I-1-2)/(I-1-8) ** according to the invention | 20 | 10 | 100 |

* The mixture tested of compound (I-1-1)/compound (I-1-7) comprised about 85% of compound (I-1-1) and about 15% of compound (I-1-7).
** The mixture tested of compound (I-1-2)/compound (I-1-8) comprised about 84% of compound (I-1-2) and about 15% of compound (I-1-8).

Example No. E

*Diabrotica balteata* Test on Maize; Drench Application

Solvent: 7 parts by weight of dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

Maize plants (*Zea mays*) are watered with the solution of the product in question and infested with larvae of the banded cucumber beetle (*Diabrotica baltenta*).

After 8 days, the activity in % is determined. 100% means that all caterpillars have been killed; 0% means that none of the caterpillars have been killed.

In this test, the following product showed good systemic action:

TABLE E

Diabrotica balteata on maize

| Active compound | Concentration (ppm) | Time at which the mortality is determined/days after treatment | % Activity (according to Abbott) |
|---|---|---|---|
| I-1-62 according to the invention | 20 | 8 | 100 |
| I-1-66 according to the invention | 20 | 8 | 90 |
| I-1-68 according to the invention | 20 | 8 | 100 |
| I-1-69 according to the invention- | 20 | 8 | 100 |
| (I-1-1)/(I-1-7) * according to the invention | 20 | 8 | 100 |
| (I-1-2)/(I-1-8) ** according to the invention | 20 | 8 | 100 |
| I-1-1 according to the invention | 20 | 8 | 100 |

* The mixture tested of compound (I-1-1)/compound (I-1-7) comprised about 95% of compound (I-1-1) and about 5% of compound (I-1-7).
** The mixture tested of compound (I-1-2)/compound (I-1-8) comprised about 95% of compound (I-1-2) and about 5% of compound (I-1-8).

Example No. F

Phytotonic Effects

Seeds of monocotyledonous and dicotyledonous crop plants were placed in sandy loam in wood-fibre pots, covered with soil and cultivated in a greenhouse under good growth conditions. The test plants were treated at the early leaf stage (BBCH10-BBCH13).

To ensure uniform water supply before commencement of stress, the potted plants were supplied with the maximum amount of water immediately beforehand by dam irrigation and, after application, transferred in plastic inserts in order to prevent subsequent, excessively rapid drying. The active compound according to the invention is sprayed onto the green parts of the plants as an aqueous suspension at an application rate of 600 l of water/ha (converted) with addition of 0.2% wetting agent (Agrotin). Substance application is followed immediately by stress treatment of the plants (drought stress).

Drought stress was induced by gradual drying out under the following conditions:

"day": 12 hours with illumination at 26° C.

"night": 12 hours without illumination at 18° C.

The duration of the drough stress phase was guided mainly by the state of the untreated (=treated with blank formulation without test compound), stressed control plants and thus varied from crop to crop from 5 to 7 days.

The end of the stress phase was followed by an approx. 7-day recovery phase, during which the plants were once again kept under good growth conditions in a greenhouse.

After the stress phase had ended (after re-irrigation) and after the recovery phase, the intensities of damage were rated in visual comparison to untreated, unstressed controls of the same age (in the case of drought stress). The intensity of damage was first assessed as a percentage (100%=plants have died, 0%=like control plants). These values were then used to calculate the efficacy of the test compounds (=percentage reduction in the intensity of damage as a result of substance application) by the following formula:

$$EF = \frac{(DV_{us} - DV_{ts})}{DV_{us}} \times 100$$

EF: efficacy (%)

$DV_{us}$: damage value of the untreated, stressed control $DV_{ts}$: damage value of the plants treated with test compound Here, an efficacy of 100% means that all treated plants are healthy and an efficacy of 0% means that the treated plants have died.

TABLE F - 1

| Active compound | Concentration in g/ha | Efficacy on wheat in % 8$^d$ after the end of the stress phase |
|---|---|---|
| (I-1-1)/(I-1-7) * | 500 | 38 |
| | | Efficacy on oilseed rape in % 9$^d$ after the end of the stress phase |
| (I-1-1)/(I-1-7) * | 500 | 40 |
| | | Efficacy on maize in % 9$^d$ after the end of the stress phase |
| (I-1-1)/(I-1-7) * | 500 | 25 |

* The mixture tested of compound (I-1-1)/compound (I-1-7) comprised about 95% of compound (I-1-1) and about 5% of compound (I-1-7).

The invention claimed is:

1. A method for controlling animal pests and for enhancing the stress tolerance of plants to abiotic stress comprising applying to said plants an active compound by drenching, soil mixing, furrow treatment, droplet application, in hydroponic systems, by planting hole treatment or dip application, floating or seedbox application, wherein said active compound is a compound of formula (I)

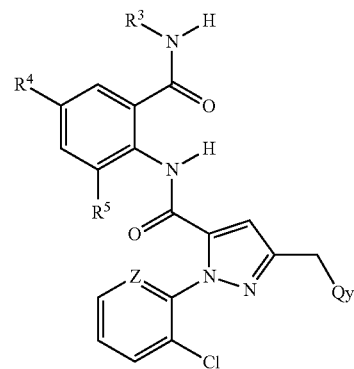

(I-1)

or an N-oxide and/or salt thereof, in which $R^3$ represents hydrogen or represents $C_1$-$C_6$-alkyl, $C_1$-$C_6$-alkoxy, $C_2$-$C_6$-alkenyl, $C_2$-$C_6$-alkynyl, $C_3$-$C_{12}$-cycloalkyl, or $C_3$-$C_{12}$-cycloalkyl-$C_1$-$C_6$-alkyl, each of which is optionally mono- or polysubstituted by identical or different substituents, where the substituents independently of one another are selected from the group consisting of amino, $C_3$-$C_6$-cycloalkylamino, halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_6$-alkoxycarbonyl, and $C_1$-$C_6$-alkylcarbonyl, or represents a 5- or 6-membered aromatic or heteroaromatic ring that contains one to three heteroatoms selected from the group consisting of O, S and N, which ring is mono- or polysubstituted by identical or different substituents independently of one another are selected from the group consisting of $SF_5$, halogen, cyano, nitro, hydroxyl, amino, carboxyl, carbamoyl, $C_1$-$C_6$-alkyl, $C_3$-$C_6$-cycloalkyl, $C_1$-$C_4$-alkoxy, $C_1$-$C_6$-haloalkyl, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_1$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_1$-$C_6$-alkoxycarbonyl, $C_1$-$C_6$-alkylcarbonyl, $C_3$-$C_6$-trialkylsilyl, $C_2$-$C_6$-alkenyl, $C_2$-$C_6$-alkynyl, $C_2$-$C_6$-haloalkenyl, $C_2$-$C_6$-haloalkynyl, $C_3$-$C_6$-halocycloalkyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, and a 3- to 6-membered ring, where the ring is optionally substituted by $C_1$-$C_6$-alkyl, halogen, cyano, nitro, halo-($C_1$-$C_6$)-alkyl, $C_1$-$C_6$-alkoxy or halo-($C_1$-$C_6$)-alkoxy, $R^4$ represents halogen, cyano, or $C_1$-$C_4$-alkyl, $R^5$ represents $C_1$-$C_6$-alkyl or halogen, Qy represents a heteroaromatic ring selected from the group consisting of

Q-58 and

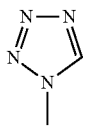

that is optionally monosubstituted by identical or different substituents independently of one another selected from the group consisting of hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, carboxyl, carbamoyl, nitro, hydroxyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)-carbonyl, ($C_1$-$C_6$-alkoxy)carbonyl, ($C_1$-$C_6$-alkyl)aminocarbonyl, di-($C_1$-$C_4$-alkyl)-aminocarbonyl, tri-($C_1$-$C_2$)alkylsilyl and ($C_1$-$C_4$-alkyl)($C_1$-$C_4$-alkoxy)imino, and Z represents N, CH, or CCl.

2. A method according to claim 1, wherein
$R^3$ represents hydrogen or represents $C_1$-$C_6$-alkyl, $C_1$-$C_6$-alkoxy, $C_2$-$C_6$-alkenyl, $C_2$-$C_6$-alkynyl, $C_3$-$C_{12}$-cycloalkyl, or $C_3$-$C_{12}$-cycloalkyl-$C_1$-$C_6$-alkyl, each of which is optionally mono- or polysubstituted by identical or different substituents, where the substituents independently of one another are selected from the group consisting of halogen, amino, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_2$-$C_6$-alkoxycarbonyl, $C_1$-$C_6$-alkylcarbonyl, $C_3$-$C_6$-cycloalkylamino and a 5- or 6-membered heteroaromatic ring, $R^4$ represents halogen, cyano or methyl,
$R^5$ represents methyl or chlorine, and
Qy represents an optionally monosubstituted heteroaromatic ring selected from the group consisting of Q-58 and Q-59, where the substituents independently of one another are selected from the group consisting of $C_1$-$C_3$-alkyl, $C_1$-$C_3$-haloalkyl, $C_1$-$C_2$-alkoxy, halogen, cyano, hydroxyl, nitro and $C_1$-$C_2$-haloalkoxy,

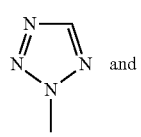 and

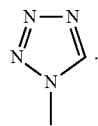

3. A method according to claim 1, where
$R^3$ represents hydrogen or represents $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, each of which is optionally mono- or polysubstituted by identical or different substituents, where the substituents independently of one another are selected from the group consisting of halogen, cyano, amino, hydroxyl, $C_1$-$C_6$-alkyl, $C_1$-$C_4$-alkoxy, $C_1$-$C_4$-haloalkoxy, $C_1$-$C_4$-alkylthio, $C_3$-$C_6$-cycloalkyl and a 5- or 6-membered heteroaromatic ring which contains 1 or 2 heteroatoms selected from the group consisting of N, O and S, where two oxygen atoms in the ring are not adjacent, $R^4$ represents halogen, cyano or methyl,
$R^5$ represents methyl,
Z represents N or CH, and
Qy represents a heteroaromatic ring selected from the group consisting of Q-58 and Q-59, which is optionally monosubstituted by methyl, ethyl, cyclopropyl, tert-butyl, chlorine, fluorine, iodine, bromo, cyano, nitro, difluoromethyl, trifluoromethyl, pentafluoroethyl, n-heptafluoropropyl or isoheptafluoropropyl,

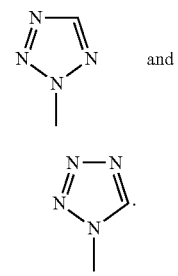

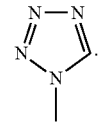

4. A method according to claim 2, in which Qy represents a mixture of Q58 and Q59, where the ratio of a compound of the formula (I) and/or N-oxides and/or salts in which Qy represents Q58 to a compound of the formula (I) in which Qy represents Q59 is from 80:20 to 99:1.

5. A method according to claim 1 where the active compound is used for enhancing plant growth or for increasing plant yield.

6. A method according to claim 1 where the abiotic stress conditions correspond to one or more conditions selected from the group consisting of drought, cold and hot conditions, osmotic stress, waterlogging, elevated soil salinity, elevated exposure to minerals, ozone conditions, strong light conditions, limited availability of nitrogen nutrients, and limited availability of phosphorus nutrients.

7. A method according to claim 1 where the active compound is used for enhancing tolerance to drought and dry conditions.

8. A method according to claim 1 where the active compound is used in combination with one or more other plant maturity-regulating compounds and/or substances which increase tolerance to abiotic stress.

9. A method according to claim 1, where the plant to be treated is selected from the group consisting of field crops, vegetables, spices, ornamental plants, shrubs, conifers, and citrus plants.

10. A transgenic plant treated by a method of claim 1.

11. A method according to claim 1 wherein the animal pests are insects and/or spider mites and/or nematodes.

12. A method according to claim 1 additionally comprising one or more other plant maturity-regulating compounds and/or substances that increase tolerance to abiotic stress.

13. A method according to claim 1 wherein the plant maturity-regulating compound is selected from the group consisting of rhizobitoxine, 2-aminoethoxyvinylglycine (AVG), methoxyvinylglycine (MVG), vinylglycine, aminooxyacetic acid, sinefungin, S-adenosylhomocysteine, 2-keto-4-methyl thiobutyrate, 2-(methoxy)-2-oxoethyl (isopropylidene)aminooxyacetate, 2-(hexyloxy)-2-oxoethyl (isopropylidene)aminooxyacetate, 2-(isopropyloxy)-2-oxoethyl (cyclohexylidene)aminooxyacetate, putrescine, spermidine, spermine, 1,8-diamino-4-aminoethyloctane, L-canaline, daminozide, methyl 1-aminocyclopropyl-1-carboxylate, N-methyl-1-aminocyclopropyl-1-carboxylic acid, 1-aminocyclopropyl-1-carboxamide, substituted 1-aminocyclopropyl-1-carboxylic acid derivatives, 1-aminocyclopropyl-1-hydroxamic acid, 1-methylcyclopropene, 3-methylcyclopropene, 1-ethylcyclopropene, 1-n-propylcyclopropene, 1-cyclopropenylmethanol, carvone, and eugenol.

14. A method according to claim 1 wherein the substance that increases tolerance to abiotic stress is a fungicide selected from the group consisting of strobilurins and succinate dehydrogenase inhibitors, an herbicide that is glyphosate, an osmolyte selected from the group consisting of glycine betaine and biochemical precursors thereof, an antioxidant selected from the group consisting of naphthols and xanthines, an azole selected from the group consisting of methylazoles and benzothiadiazole, acetylsalicylic acid, a sulphoximine selected from the group consisting of oxylipins, or an insecticide selected from the group consisting of neonicotinoids.

\* \* \* \* \*